United States Patent [19]

Muramatsu et al.

[11] Patent Number: 6,071,733
[45] Date of Patent: Jun. 6, 2000

[54] METHOD OF MAKING RECOMBINANT ENZYME

[75] Inventors: Masayoshi Muramatsu, Aichi; Ayumi Koike, Miyagi; Kyozo Ogura, Miyagi; Tanetoshi Koyama, Miyagi; Naoto Shimizu, Miyagi; Yenwin Cho, Miyagi, all of Japan

[73] Assignee: Toyota Jidosha Kabushiki Kaisha, Toyota, Japan

[21] Appl. No.: 09/217,609

[22] Filed: Dec. 22, 1998

Related U.S. Application Data

[62] Division of application No. 08/873,235, Jun. 11, 1997.

[30] Foreign Application Priority Data

Jun. 14, 1996 [JP] Japan ................................. 8-154441

[51] Int. Cl.⁷ .............................. C12N 9/10; C12N 1/20; C12N 1/00; C07H 21/04
[52] U.S. Cl. ...................... 435/193; 435/252.5; 435/832; 435/839; 536/23.2
[58] Field of Search .................................. 435/193, 183, 435/252.5, 832, 839; 536/23.2

[56] References Cited

FOREIGN PATENT DOCUMENTS

| | | |
|---|---|---|
| 0 674 000 A2 | 9/1995 | European Pat. Off. . |
| 0 173 494 A2 | 3/1996 | European Pat. Off. . |
| 0 699 761 A2 | 3/1996 | European Pat. Off. . |
| WO 95/12662 | 5/1995 | WIPO . |
| WO 95/21263 | 8/1995 | WIPO . |

OTHER PUBLICATIONS

Shimizu et al. (1996) Mechanism of isoprenoid chain elongation systems: Cloning and analysis medium–chain prenyl diphosphate synthases. Tennen Yuki Kagobutsu Toronkai Koen Yoshishu, 38th, 31–36 (abstract).

Ohnuma, et al., *J. Bio. Chem.*, 269:20, pp. 14792–14797, May 20, 1994.

Math, et al., *Proc. Natl. Acad. Sci. USA*, 89, pp. 6761–6764, Aug. 1992.

Yoshida, et al., *Biochem.*, 26:21, pp. 6840–6845,1987.

*Primary Examiner*—Ponnathapu Achutamurthy
*Assistant Examiner*—Elizabeth Slobodyansky
*Attorney, Agent, or Firm*—Kenyon & Kenyon

[57] ABSTRACT

The present invention provides a polypeptide selected from a polypeptide of subunit (A) or a polypeptide of subunit (B) of a prenyl diphosphate synthetase; a DNA coding for the polypeptide; a recombinant vector comprising the DNA; a transformant transformed with the vector; and a method for preparing an active type prenyl diphosphate synthetase. Also disclosed is a method for preparing an active type enzyme on which a specific property has been conferred, comprising mixing polypeptides of the two subunits of a heterodimeric enzyme, the polypeptides being derived from different organisms and one of the polypeptides having the specific property.

3 Claims, 13 Drawing Sheets

BIOSYNTHETIC PATHWAY OF ISOPRENOIDS

DESIGN OF PRIMERS BASED ON PRESERVED AMINO ACID SEQUENCES

PLATE TRANSFER DEVICE

METHOD OF MAKING RECOMBINANT ENZYME

This application is a division of application Ser. No. 08/873,235 filed Jun. 11, 1997 which is incorported herein in its entirety by reference thereto.

BACKGROUND OF THE INVENTION

1. Field of the Invention

The present invention relates to a method for producing the peptide of a prenyl diphosphate synthetase, a method for producing an active type prenyl diphosphate synthetase, a DNA coding for the synthetase, a recombinant vector comprising the DNA and a transformant transformed with the vector.

2. Description of the Prior Art

An extremely wide variety of isoprenoid compounds are found in natural creatures from bacteria to higher eukaryotes. For example, steroids, carotenoids, polyprenols which are sugar carriers, quinones, tRNA modified with isopentenyladenine, prenylated proteins and the like may be enumerated. All of these isoprenoids are biosynthesized through prenyl diphosphate as an intermediate which is produced by a prenyl diphosphate synthetase (FIG. 1).

The "prenyl diphosphate synthetase" is a general term for those enzymes which catalyze a reaction that condensation-polymerizes prenyl diphosphate (an allylic primer) and 3-isopentenyl diphosphate (IPP) to produce polyprenyl diphosphate.

Prenyl diphosphate synthetases are divided into two groups. One group consists of enzymes that catalyze a condensation reaction in which the double bond formed by each condensation of IPP is of E type. The other group consists of enzymes that catalyze a condensation reaction in which the double bond formed by each condensation of IPP is of Z type. Further, the maximum length of the isoprene chain which each prenyl diphosphate synthetase can produce is fixed. Since the hydrophobic property of a product varies depending of the isoprene chain length of the product, there is great difference in the mode of requirement for the activity of enzymes. When bacterial enzymes are compared in terms of the mode of requirement, prenyl diphosphate synthetases are classified into the following four groups.

(1) Prenyl diphosphate synthetase I (E type, short chain prenyl diphosphate synthetase)
  (i) Geranyl diphosphate (GPP) synthetase (Sagami, H. et al., (1978) Biochem. Biophys. Res. Commun., 85, 575) ($C_5 \rightarrow C_{10}$)
  The expression "$C_5 \rightarrow C_{10}$" means that the subject synthetase catalyzes the synthesis from a compound with 5 carbon atoms to a compound with 10 carbon atoms (hereinafter, this indication has a similar meaning.)
  (ii) Farnesyl diphosphate (FPP) synthetase (Takahashi, I. and Ogura, K., (1981) J. Biochem. 89, 1581; Fujisaki, S. et al., (1986) J. Biochem., 99, 1327) ($C_5 \rightarrow C_{15}$)
  (iii) Geranylgeranyl diphosphate (GGPP) synthetase (Takahashi, I. and Ogura, K., (1982) J. Biochem. 92, 1527; Sagami, H. and Ogura, K., (1981) J. Biochem., 89, 1573) ($C_5 \rightarrow C_{20}$)

(2) Prenyl diphosphate synthetase II (E type, medium chain prenyl diphosphate synthetase)
  (i) Hexaprenyl diphosphate (HexPP) synthetase (Fujii, H. et al., (1982) J. Biol. Chem., 257, 14610) ($C_{15} \rightarrow C_{30}$)
  (ii) Heptaprenyl diphosphate (HepPP) synthetase (Takahashi, I. et al., (1980) J. Biochem., 255, 4539) ($C_{15} \rightarrow C_{35}$)

(3) Prenyl diphosphate synthetase III (E type, long chain prenyl diphosphate synthetase)
  (i) Octaprenyl diphosphate (OctPP) synthetase (Fujisaki, S. et al., (1986), J. Biochem., 99, 1327) ($C_{15} \rightarrow C_{40}$)
  (ii) Nonaprenyl diphosphate (NonPP) synthetase (Sagami, H. et al., (1977) Biochemistry, 16, 4616) ($C_{10} \rightarrow C_{45}$) Decaprenyl diphosphate (DecPP) synthetase (Ishii, K. et al., (1983) Biochem. Biophys. Res. Commun., 116, 500) ($C_{15} \rightarrow C_{50}$)

(4) Prenyl diphosphate synthetase IV (Z type, long chain prenyl diphosphate synthetase)
  (i) Z-nonaprenyl diphosphate synthetase (Ishii, K. et al., (1986) Biochem. J., 233, 773) ($C_{15} \rightarrow C_{45}$)
  (ii) Undecaprenyl diphosphate (UPP) synthetase (Takahashi, I. and Ogura, K. (1982) J. Biochem., 92, 1527; Keenman, M. V. and Allen, C. M. (1974) Arch. Biochem. Biophys., 161, 375) ($C_{15} \rightarrow C_{55}$)
  (iii) Dehydrodolichyl diphosphate (deDolPP) synthetase (Sagami, H. et al., (1989) Biochem. Biophys. Acta. 1002, 218) ($C_{15} \rightarrow C_{85-105}$)

Prenyl diphosphate synthetase I successively condensates 3-isopentenyl diphosphate (IPP) with dimethylallyl diphosphate (DMAPP) generated by isomerization of IPP as an allylic primer to thereby synthesize a short chain, totally E type prenyl diphosphate with 20 or less carbon atoms. This product serves as a precursor for steroids, carotenoids or prenylated proteins. Further, geranyl diphosphate (GPP), farnesyl diphosphate (FPP) and geranylgeranyl diphosphate (GGPP) also serve as an allylic primer substrate for a medium- or long-chain prenyl diphosphate synthetase.

Hexaprenyl diphosphate synthetase (HexPS) and heptaprenyl diphosphate synthetase (HepPS) belong to prenyl diphosphate synthetase II. These enzymes synthesize hexaprenyl diphosphate and heptaprenyl diphosphate, respectively, without DMAPP nor GPP as a primer but using FPP as an allylic primer. The products are highly hydrophobic and serve as precursors for the side chains of menaquinones or ubiquinones in organisms having these enzymes. These prenylquinones play important roles in the respiratory chain or the electron transport system in photosynthesis.

Any member of prenyl diphosphate synthetase II is an enzyme composed of two essential proteins which do not have the catalytic activity independently. However, the enzyme has a property that in the presence of substrates for the enzyme, the two proteins associate with each other and exhibit the catalytic activity (Yoshida, I. et al., (1989) Biochem. Biophys. Res. Commun., 160, 448). In this point, the enzyme of this group is greatly different from other prenyl diphosphate synthetase.

As a microorganism producing prenyl diphosphate synthetase II, *Micrococcus luteus, Bacillus subtilis* and the like are known (Fujii, H. et al., (1982) J. Biol. Chem., 257, 14610; Takahashi, I. et al., (1980) J. Biol. Chem., 255, 4539). The following facts have been shown on the two components (designated "component A" and "component B") of HexPS from *Micrococcus luteus* B-P 26 and on the two components (designated "component I" and "component II") of HepPS of *Bacillus subtilis*.

a) Component A and component I are relatively high in thermostability, whereas component B and component II have thermostability as low as that of other enzymes derived from mesophiles (Fujii, H. et al., (1982) J. Biol. Chem., 257, 14610).

b) There is no interchangeability between component A and component I. In other words, neither a combination of component A and component II nor a combination of component I and component B exhibits enzyme activity (Fujii, H. et al., (1983) FEBS Lett., 161, 257).

c) Component B and component II are affected by SH reagent and arginine-specific reagent to lower the enzyme activity remarkably, whereas component A and component I are not affected by these reagents (Yoshida, I. et al., (1989) Biochem. Biophys. Acta, 995, 138).

Octaprenyl diphosphate synthetase (OctPS), nonaprenyl diphosphate synthetase (NonPS) and the like belong to prenyl diphosphate synthetase III. Like prenyl diphosphate synthetase I, these enzymes are a homodimeric protein composed of identical subunits. They exhibit the catalytic activity by themselves. However, in order to maintain the turnover as a catalyst, they require a proteinaceous factor which removes hydrophobic products from their active site (Ohnuma, S. et al., (1991) J. Biol. Chem., 266, 23706). This activator is interchangeable and exhibits activating action against any enzyme belonging to prenyl diphosphate synthetase III (Ohnuma, S. et al., (1991) J. Biol. Chem., 266, 23706).

Enzymes belonging to prenyl diphosphate synthetase IV condensate IPP in the Z-structual form to synthesize polyprenyl diphosphate of E- and-Z mixed type using a short-chain prenyl diphosphate (GPP, FPP) as a primer substrate. Bacterial undecaprenyl diphosphate synthetase (UPS) and eukaryotic dehydrodolichyl diphosphate synthetase (deDolPS) are included in this group. A large number of these enzymes are a membrane-bound protein and when solubilized with a surfactant or the like, they require the addition of a surfactant such as Triton X-100 for the manifestation of their activity in almost all cases (Takahashi, I and Ogura, K. (1982) J. Biochem., 92, 1527; Allen, C. M. and Muth, J. D. (1977) Biochemistry, 16, 2908). Additionally, the activator common in prenyl diphosphate synthetase III is ineffective against UPS. It is considered that this fact is because hydrophobic environment of a membrane is essential for the manifestation of the enzyme activity.

The most part of the above-described information has been obtained from experiments using those enzymes extracted and purified from a solution of disrupted cells. In order to clarify a more detailed enzyme reaction mechanism, not only the primary structure but also the crystal structure of enzyme proteins should be analyzed. For this purpose, the cloning of genes coding for these enzyme proteins is indispensable.

Actually, prenyl diphosphate synthetase genes such as FPS and GGPS have been cloned recently one by one (FPP synthetases: Koyama, T. et al., (1993) J. Biochem., 113, 355; Fujisaki, S. et al., (1990) J. Biochem., 108, 995; Anderson, M. A. et al., (1989) J. Biol. Chem., 264, 19176; Clarke, C. F. et al., (1987) Mol. Cell. Bio., 7, 3138; Wilkin, D. J. et al., (1990) J. Biol. Chem., 265, 4607; GGPP synthetases: Carattoli, A. et al., (1991) J. Biol. Chem., 266, 5854; Armstrong, G. A. et al., (1990) Proc. Natl. Acad. Sci. USA, 87, 9975; Math, S. K. et al., (1992) Proc. Natl. Acad. Sci. USA, 89, 6761; Misawa, N. et al., (1990) J. Bacteriol., 172, 6704). With respect to HexPP synthetase, a gene coding for one of the two components (corresponding to "component B" described previously) has been cloned by an experiment on complementarity in yeast. However, the two components of this synthetase are necessary for the manifestation of the activity, as described previously. Therefore, it cannot be said that a perfect cloning of the gene coding for the enzyme of active type has been performed (HexPP synthetase: Ashby, M. M. and Edwards, P. A. (1990) J. Biol. Chem., 265, 13157).

The present inventor has compared the primary structures of the above-mentioned enzymes based on the base sequences for their genes. As a result, it has become clear that prenyl diphosphate synthetases have 7 regions in which the amino acid sequence has been relatively preserved beyond the difference in chain length or organism species (Koyama, T. et al., (1993) J. Biochem. 113, 355–363). Since these regions are preserved in a group of enzymes which catalyze substantially the same reaction, they are believed to have an important role in the catalytic function. On the other hands, it is predicted that non-preserved regions have a portion defining the chain length, a portion involved in the difference in the mode of manifestation of the enzymatic function, and the like. However, at present, the number of cloned genes of prenyl diphosphate synthetases having different chain length is too small to find out the existence of such portions from comparison of primary structures.

From the viewpoint of the manifestation of enzymatic function, enzymes belonging to prenyl diphosphate synthetase II are greatly different from other prenyl diphosphate synthetases, as described previously. They are characterized by being composed of two proteins (heterodimeric type), each of which does not have a catalytic function alone but which associate with each other in the presence of a substrate to exhibit a catalytic function.

Substances synthesized by these heterodimeric prenyl diphosphate synthetases are precursors of those substances such as vitamin K and ubiquinones which exist universally in organisms and, thus, they are important physiologically active substances. Therefore, they are of high utility value. Furthermore, the prenyl diphosphate produced by a heterodimeric prenyl diphosphate synthetase is industrially extremely useful since the chain length and structural isomers thereof can be strictly controlled. Thus, the expression of such a synthetase in large quantity is needed.

Accordingly, it is desired to isolate genes coding for the two proteins of an enzyme belonging to prenyl diphosphate synthetase II, to express the genes separately and thereby to produce the proteins in large quantity.

OBJECTS AND SUMMARY OF THE INVENTION

It is an object of the invention to provide a method for producing peptides of prenyl diphosphate synthetases, a method for producing an active type prenyl diphosphate synthetase, a DNA coding for the synthetase, a recombinant vector comprising the DNA and a transformant transformed with the vector.

As a result of extensive and intensive researches toward the solution of the above assignment, the present inventor has succeeded in cloning the gene of a prenyl diphosphate synthetase from *Micrococcus luteus* and also succeeded in preparing an active type prenyl diphosphate synthetase by mixing peptides of the individual subunits of a prenyl diphosphate synthetase. Thus, the present invention has been achieved.

The present invention relates to a DNA coding for a polypeptide selected from a polypeptide of subunit (A) of a prenyl diphosphate synthetase or a polypeptide of subunit (B) thereof.

Subunit (A) and Subunit (B) are two polypeptide chains which form a heterodimer to express prenyl diphosphate synthetase activity. Of these chains, Subunit (B) has an amino acid sequence characteristic of prenyl transferase.

As the polypeptide of subunit (A), a polypeptide represented substantially by the amino acid sequence shown in SEQ ID NO: 1 may be given. As the polypeptide of subunit (B), a polypeptide represented substantially by the amino acid sequence shown in SEQ ID NO: 2 may be given. As the DNA coding for the polypeptide of subunit (A), the DNA represented by SEQ ID NO: 3 may be given. As the DNA coding for the polypeptide of subunit (B), the DNA represented by SEQ ID NO: 4 may be given.

The term "substantially" used herein means that, as long as a polypeptide selected from a polypeptide of subunit (A) or a polypeptide of subunit (B) has activity to synthesize prenyl diphosphate, the amino acid sequence for this polypeptide may have variations such as deletion, substitution, insertion, or the like.

Accordingly, for example, the amino acid sequence of SEQ ID NO: 1 having a deletion of methionine (Met) at position 1 is included in the above-mentioned amino acid sequence having variations. Also, not only the base sequence coding for the amino acids contained in the polypeptide of the invention, but also a degeneracy isomer of the above base sequence different only in degenerate codons is included in the DNA of the present invention.

The present invention further relates to a recombinant vector comprising the DNA described above.

The present invention further relates to a transformant obtained by transforming a host organism with the recombinant vector described above.

The present invention further relates to a method for producing a polypeptide of subunit (A) and/or a polypeptide of subunit (B) comprising culturing the transformant described above in a medium to thereby accumulate the polypeptide of subunit (A) and/or the polypeptide of subunit (B) in the culture and collecting the polypeptide(s).

The present invention further relates to a polypeptide selected from the polypeptide of subunit (A) represented substantially by SEQ ID NO: 1 and the polypeptide of subunit (B) represented substantially by SEQ ID NO: 2.

The present invention further relates to a method for producing an active type prenyl diphosphate synthetase comprising preparing peptides of the individual subunits of a heterodimeric prenyl diphosphate synthetase by recombinant DNA techniques and mixing the resultant peptides of the individual subunits. As peptides of the individual subunits, the polypeptide of subunit (A) and the polypeptide of subunit (B) represented by, for example, SEQ ID NO: 1 and SEQ ID NO: 2, respectively, may be given.

The present invention further relates to a method for producing an active type enzyme comprising preparing separately polypeptides of the two subunits of a heterodimeric enzyme, the polypeptides being derived from different organisms (e.g., microorganisms) and one of the polypeptides having a specific property, and mixing the resultant polypeptides for these subunits to thereby obtain an active enzyme on which the specific property has been conferred. In this method, as one of the polypeptides for the two subunits, the polypeptide derived from *Bacillus subtilis* and represented substantially by the amino acid sequence of SEQ ID NO: 5 may be given. As the other polypeptide, the polypeptide derived from *Bacillus stearothermophilus* and represented substantially by the amino acid sequence of SEQ ID NO: 6 may be given. As the active type enzyme on which the specific property has been conferred, a thermoresistant, active type prenyl diphosphate synthetase may be given.

The present invention further relates to a method for preparing an active type prenyl diphosphate synthetase comprising mixing the polypeptide of a subunit of a *Bacillus subtilis*-derived prenyl diphosphate synthetase represented substantially by the amino acid sequence of SEQ ID NO: 5 and the polypeptide of a subunit of a *Bacillus stearothermophilus*-derived thermoresistant prenyl diphosphate synthetase represented substantially by the amino acid sequence of SEQ ID NO: 6 to thereby obtain a heterodimeric, active type prenyl diphosphate synthetase having thermal resistance and enhanced activity.

DETAILED DESCRIPTION OF THE INVENTION

Figure 1:
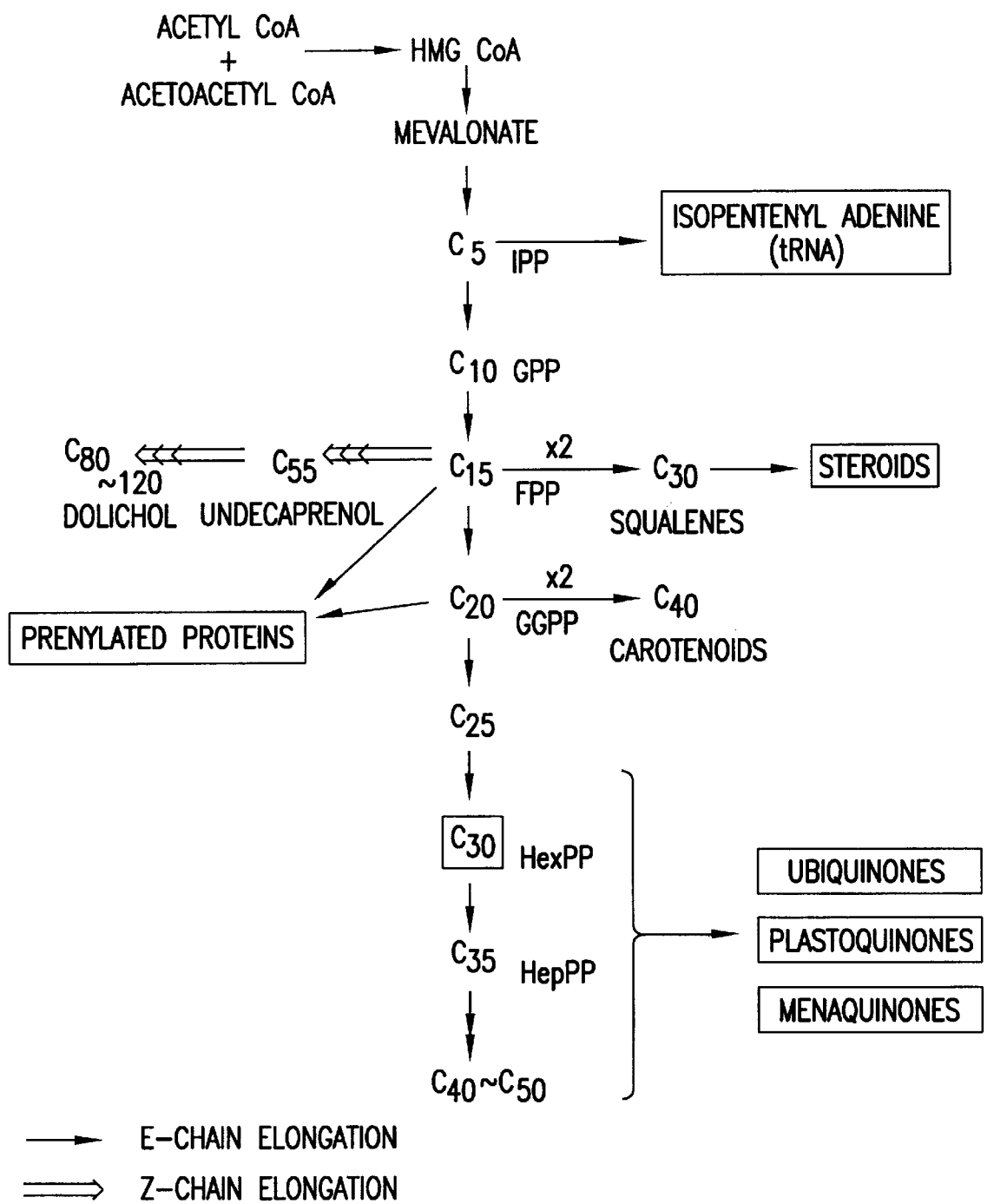
FIG. 1 is a chart showing the biosynthetic pathway of isoprenoids.

Hereinbelow, the present invention will be described in detail.

Prenyl diphosphate synthetases have 7 regions in which the amino acid sequence has been relatively preserved beyond the difference in enzymes or organism species. It is expected that these regions are also preserved in the hexaprenyl diphosphate synthetase of *Micrococcus luteus* B-P 26 (obtained from Dr. L. Jeffries, Walton Oaks Experimental Station Vitamins, Ltd.; hereinafter referred to as "*M. luteus* B-P 26").

Then, in the present invention, the prenyl diphosphate synthetase gene of *M. Luteus* B-P 26 is cloned using recombinant DNA techniques based on the preserved amino acid sequences of bacterial prenyl diphosphate synthetases.

Hereinbelow, techniques for DNA cloning will be described.

First, genomic DNA is prepared from a prenyl diphosphate synthetase producing bacterium, for example, cultured cells of *M. luteus* B-P 26. Subsequently, DNA probes are synthesized based on the 7 regions in which the amino acid sequence is relatively preserved beyond the difference in the kind of prenyl diphosphate synthetase and microorganism species and colony hybridization or the like is performed using these probes, to thereby clone a full length gene of interest.

(1) Preparation of Genomic DNA

The cultivation of *M. luteus* B-P 26 may be performed by conventional methods. For example, *M. luteus* B-P 26 is inoculated into a medium containing 0.5% yeast extract, 1% polypeptide and 1% sodium chloride and cultured at 30–37° C. for 1–3 days. In order to prepare genomic DNA from cultured cells of *M. luteus* B-P 26, any known technique may be used. For example, the cells are treated with lysozyme and then treated with a surfactant such as sodium lauryl sulfate. Thereafter, proteins are removed from the cell lysate with an organic solvent such as phenol, chloroform, ether, or the like, and then the lysate are subjected to ethanol precipitation. Thus, genomic DNA can be prepared easily by conventional methods (J. Mol. Biol., 3, 208, 1961).

Subsequently, the genomic DNA obtained is ligated to vector plasmids to prepare a genomic DNA library. This may be performed by conventional methods. For example, genomic DNA chains and plasmid DNA chains are digested with an appropriate restriction enzyme (e.g., EcoRI, BamHI, HindIII, Sau3AI, MboI, PstI), and then the resultant DNA fragments are treated with a DNA ligase (e.g., T4 DNA ligase) or, depending on the state of the digested ends, with a terminal transferase or DNA polymerase. Thereafter, the DNA fragments are ligated using a DNA ligase (Molecular Cloning, Cold Spring Harbor Laboratory, 269, 1982; Method in Enzymol., 68, 41, 1979). As the vector used here, aλ phage vector (λ gt10, Charon 4A, EMBL-3, etc.), a plasmid vector (pBR322, pSC101, pUC19, pUC119, pACYC117) and the like may be enumerated. The DNA fragments described above are incorporated in these vectors, which are used to transform a host organism such as *Escherichia coli* (e.g., DH1, HB101, JM109, C600, MV1184, TH2) to thereby obtain a genomic DNA library.

(2) Preparation of Probes for Screening

Figure 2:
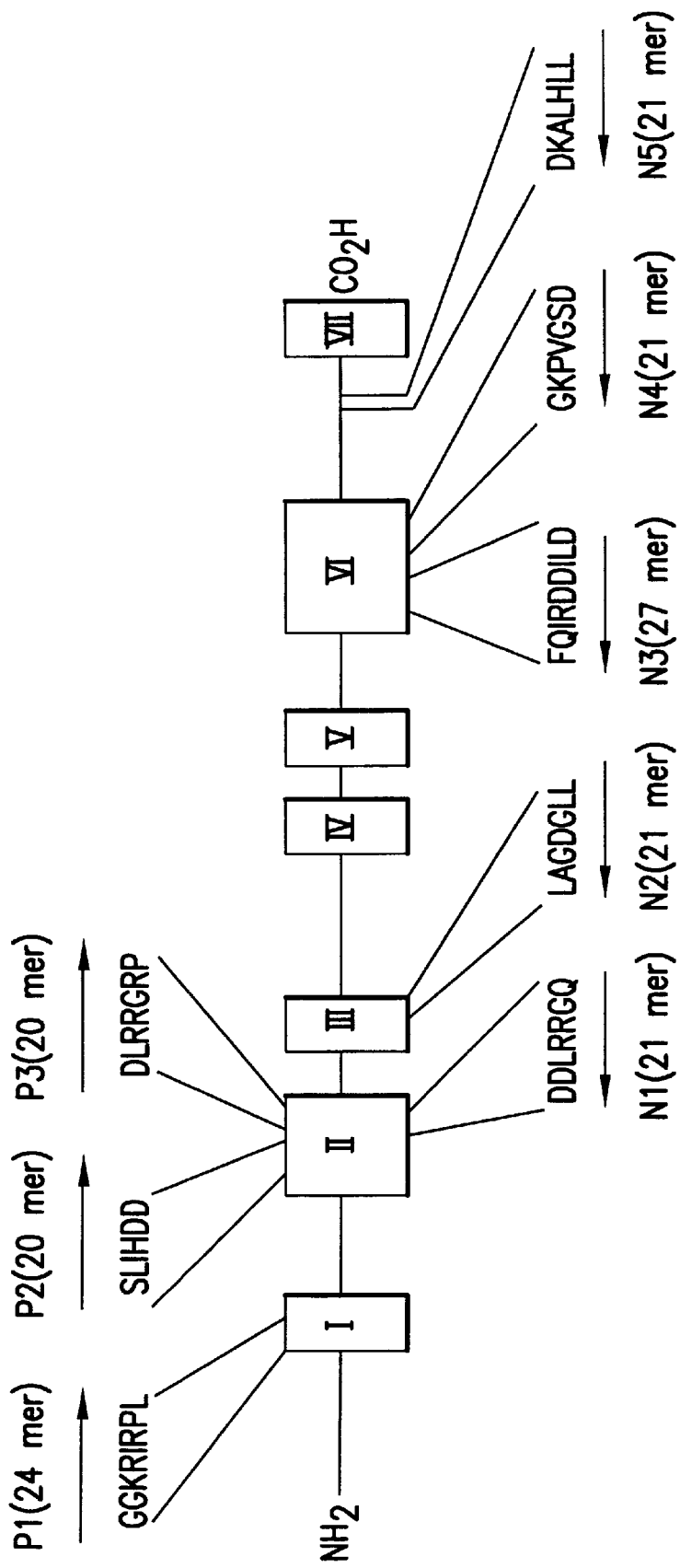
FIG. 2 shows the designing of primers based on preserved amino acid sequences.

First, probes for screening the above genomic DNA by hybridization are prepared. In order to prepare higher selective probes, it is considered appropriate to prepare oligonucleotides coding for those regions in which amino acid residues are highly preserved among different species of organisms. Probes may be prepared by conventional chemical synthesis. As the amino acid sequence which satisfies the above condition, the following preserved amino acid sequences are selected [the underlined amino acids are preserved more than 50% in different species of organisms (see below)] (FIG. 2).

The sequence "Gly Gly Lys Arg Ile Arg Pro Leu" (SEQ ID NO: 7) in Region I

The sequence "Ser Leu Ile His Asp Asp" (SEQ ID NO: 8) and the sequence "Asp Leu Arg Arg Gly Arg Pro" (SEQ ID NO: 9) in Region II The sequence "Leu Ala Gly Asp Gly Leu Leu" (SEQ ID NO: 10) in Region III The sequence "Phe Gln Ile Arg Asp Asp Ile Leu Asp" (SEQ ID NO: 11) and the sequence "Gly Lys Pro Val Gly Ser Asp" (SEQ ID NO: 12) in Region VI.

Regions I, II, III and VI used herein correspond to the regions of positions 39–52, positions 73–103, positions 115–123 and positions 217–250, respectively, in the amino acid sequence for a *Bacillus stearothermophylus*-derived FPS described by Koyama, T. et al., J. Biochem. 113, 355–363 (1993).

The examination of preserved amino acid sequences among different organism species can be made among FPSs from *Bacillus stearothermophylus, Escherichia coli, Saccharomyces cerevisiae*, rat and human; GGPSs from *Erwinia herbicola* and *Erwinia uredovora*; and HexPS from *Saccharomyces cerevisiae*. The design of probes is performed based on the amino acid sequences for the 7 regions of *Bacillus stearothermophylus* which belongs to Gram positive bacteria as *M. luteus* B-P 26 does.

Based on these amino acid sequences, the following oligonucleotide probes are prepared.

P1: SEQ ID NO: 13
P2: SEQ ID NO: 14
P3: SEQ ID NO: 15
N1: SEQ ID NO: 16
N2: SEQ ID NO: 17
N3: SEQ ID NO: 18
N4: SEQ ID NO: 19
N5: SEQ ID NO: 20

Using the genomic DNA described previously as a template and above oligonucleotides as probes, hybridization is performed.

(3) Screening

The screening of a hexaprenyl diphosphate synthetase gene from the genomic DNA of *M. luteus* B-P 26 may be performed by conventional methods, for example, Southern hybridization, colony hybridization, and the like.

The present inventor has cloned an FPS gene of *M. luteus* B-P 26 by the method described in Example 2 later. Accordingly, the location of the FPS gene can be easily identified by radio-labelling a DNA fragment thereof designated B500 (SEQ ID NO: 28) and performing Southern hybridization. As seen in these results, the inventor has thought that if there exist in the HexPS gene DNA sequences coding for the preserved amino acid sequences in prenyl diphosphate synthetases, those DNA fragments which are probe-positive and not derived from the FPS gene can be selected.

Then, in the present invention, Southern hybridization of the genomic DNA of *M. luteus* B-P 26 was performed using the probes prepared as described above.

Briefly, the genomic DNA of *M. luteus* B-P 26 is digested with appropriate restriction enzymes (EcoRI, HindIII, PstI) separately. The resultant restriction fragments are electrophoresed on agarose gel. Then, the gel is treated with alkali to denature the DNA into single-stranded DNA, and is transferred to a nylon membrane. This nylon membrane is UV-irradiated to fix the DNA on the membrane. Subsequently, hybridization is performed using a labeled probe or B500 as a probe. After washing, autoradiography is performed with a bio-image analyzer to thereby confirm the location of those DNA bands having homology to the probe.

Probes (P1, P2, N3, N4 and N5) are end-labeled with $^{32}$P by enzymatically transferring the phosphate group from [$\gamma$-$^{32}$P]ATP to the 5' end. On the other hand, B500 is $^{35}$S-labeled with [$\alpha$-$^{35}$S]dCTP by the random prime labeling method to obtain a probe.

(4) Cloning of DNA Fragments Weakly Hybridizing with Probe B500

The probe B500 is a DNA fragment containing a portion of the FPS gene of *M. luteus* B-P 26, as described previously. Therefore, this probe strongly hybridizes with the FPS gene. Also, B500 contains DNA sequences coding for the preserved amino acid sequences among prenyl diphosphate synthetases. If the HexPS gene of interest has DNA sequences coding for the preserved amino acid sequences among prenyl diphosphate synthetases, such DNA sequences also hybridize with B500.

Then, in order to screen a gene coding for the peptide of a prenyl diphosphate synthetase of the invention, the cloning of those DNA fragments weakly hybridizing with B500 other than those DNA fragments strongly hybridizing with B500 because of the presence of the FPS gene is performed.

EcoRI-digested genomic DNA fragments 4–6 kbp in size are extracted from agarose gel and inserted into pUC119. *E. coli* strain JM109 is transformed with the resultant plasmid to thereby prepare a DNA library covering this region. Then, colony hybridization is performed using each probe.

The resultant clones are cultured in an appropriate medium (e.g., LB liquid medium). Then, cells of each clone are harvested and disrupted by sonication, to thereby obtain a crude enzyme extract. HexPS activity is determined using this crude enzyme extract.

Thus, a clone containing the prenyl diphosphate synthetase gene is obtained, and this clone is used for the DNA sequencing.

(5) Determination of the DNA Sequence

The resultant clone is digested with an appropriate restriction enzyme and electrophoresed on agarose gel, to thereby prepare a restriction map from the migration pattern and migration distance.

Based on this restriction map, the deletion of DNA fragment (i.e., making into smaller fragments) is performed. Thus, the smallest clone exhibiting activity is obtained, and the DNA sequence for the smallest clone exhibiting activity is analyzed.

The sequence may be determined using deletion clones which contain the insert DNA having a deletion of about 200 bp at both ends in opposite directions.

The screened clone is digested with an appropriate restriction enzyme (e.g., EcoRI, PstI) and cloned into a plasmid such as pUC119, pUC19 or the like. Then, the DNA sequence of interest may be determined by conventional base sequence analysis methods such as the dideoxy method by Sanger et al. (Proc. Natl. Acad. Sci. USA, 74, 5463 (1977)). The determination of the DNA sequence may be performed with an automatic base sequence analyzer using such as T7 Sequencing Kit (Pharmacia).

Once the DNA sequence is thus determined, the DNA of interest can be obtained by hybridization using a DNA fragment obtained from such as chemical synthesis or PCR.

The DNA of the invention may be used as a gene to express a prenyl diphosphate synthetase.

As the thus determined DNA sequence for a DNA coding for the polypeptide of a subunit of the prenyl diphosphate synthetase, the base sequence shown in SEQ ID NO: 21 may be given, for example. This base sequence contains 3 open reading frames (ORFs) designated hex1, hex2 and hex3. These ORFs correspond to positions 216–644 (SEQ ID NO: 3), positions 622–1359 (SEQ ID NO: 29) and positions 1368–2342 (SEQ ID NO: 4), respectively, in the DNA sequence shown in SEQ ID NO: 21.

The ORFs described above may be cloned as a whole or cloned individually by conventional recombinant DNA techniques. For example, the DNA coding for the polypeptide of a subunit of the prenyl diphosphate synthetase may be digested with an appropriate restriction enzyme to thereby generate three DNA fragments each containing hex1, hex2 or hex3, which are individually ligated to a plasmid vector digested with the same restriction enzyme. Thus, individual ORFs may be cloned.

(6) Identification of Prenyl Diphosphate Synthetase Genes

In order to examine whether the three polypeptides obtained by the expression of the three genes described above have activity or not, plasmids each containing one of the ORFs are prepared and a host cell is transformed with each of the plasmids. The resultant transformant is cultured to thereby prepare a crude enzyme extract. Then the enzyme activity of prenyl diphosphate synthetase is examined using this crude extract.

The transformation of a host cell with a recombinant vector may be performed by, for example, adding a recombinant vector to competent cells prepared with $CaCl_2$, $MgCl_2$ or RbCl (when the host cell is *E. coli*).

In order to detect cells containing the gene of interest, the colony or plaque hybridization method (J. Sambrook, E. F. Fritsch and T. Maniatis, Molecular Cloning, Cold Spring Harbor Laboratory Press) using oligonucleotide probes chemically synthesized based on the amino acid sequence for the protein, or the like may be used.

The fragments containing the thus cloned DNAs coding for the polypeptides of the prenyl diphosphate synthetase may be individually re-incorporated into an appropriate vector (e.g., pMalc2, pTrc99A) to thereby express the genes highly in *E. coli* cells. Further, by re-incorporating the fragment into an appropriate vector, it is possible to transform other procaryotic or eucaryotic host cell with the vector. Further, by introducing into such a vector an appropriate promoter and sequences involved in phenotypic expression, the gene can be expressed in each host cell.

As a host cell, mammal-derived cells such as COS cells, Chinese hamster ovary (CHO) cells, HELA cells (human cervical carcinoma cells), mouse Sertoli's cells; insect-derived cells; and yeast-derived cells such as *Pichia pastolis* and *Saccharomyces cerevisiae* may be enumerated. As a vector to transform these cells, BacPAK6, pSVL, SV40 and the like may be enumerated. These vectors contain a replication origin, selectable marker, promoter, polyadenylation signal and the like.

As a promoter for gene expression, a promoter from retrovirus, polyoma virus or the like may be used.

As a replication origin, one from SV40, polyoma virus, adenovirus, VSV, etc. may be used. As a selectable marker, a thymidine kinase gene, a dihydrofolate reductase gene or the like may be used.

(7) Expression of Polypeptides

In order to accumulate the polypeptide of subunit (A) and/or the polypeptide of subunit (B) of a prenyl diphosphate synthetase in a culture using the above-mentioned host-vector system and to collect the polypeptide(s), the host cell is transformed with a recombinant DNA obtained by incorporating the gene of interest in an appropriate site in the vector and then the resultant transformant is cultured. Further, in order to separate and purify the peptide(s) from cells or culture solution, known techniques may be used. For example, salting out, gel filtration, ion exchange chromatography, affinity chromatography, reversed phase chromatography, and the like may be used for purification independently or in combination. Whether the purified polypeptide is the polypeptide of interest or not may be confirmed by SDS polyacrylamide gel electrophoresis, Western blotting, or the like.

(8) Production of a Heterodimeric, Active Type Prenyl Diphosphate Synthetase

According to the present invention, an active type prenyl diphosphate synthetase can be produced by preparing the peptides of the individual subunits of a heterodimeric prenyl diphosphate synthetase by recombinant DNA techniques and mixing the resultant peptides of the individual subunits.

For example, as subunit (A) of a prenyl diphosphate synthetase, the expression product of hex1 may be given, and as subunit (B) the expression product of hex3. By mixing the expression product of hex1 and the expression product of hex3, an active type prenyl diphosphate synthetase having high enzyme activity can be obtained.

It should be noted that a mixture of the expression product of hex1 (subunit (A)) and the expression product of hex2 nor a mixture of the expression product of hex3 (subunit (B)) and the expression product of hex2 does not have the enzyme activity of prenyl diphosphate synthetase.

According to the present invention, an active type enzyme on which a specific property has been conferred can be produced by preparing separately the polypeptides of the two subunits of a heterodimeric enzyme, the polypeptides being derived from different organisms and one of the polypeptides having the specific property, and mixing the resultant polypeptides of these subunits.

The term "specific property" used herein means a specific property other than the enzymatic activity of the enzyme conferred on the enzyme additionally. For example, thermal resistance, alkali resistance, acid resistance, long term storage stability, resistance to organic solvents, and the like may be enumerated.

In the present invention, increase in specific activity can also be achieved in addition to those specific properties.

As a specific example for such an enzyme, a heterodimeric, active type prenyl diphosphate synthetase having a conferred thermal resistance and enhanced activity may be given which is obtained by mixing equal amounts of a polypeptide of a subunit of a prenyl diphosphate synthetase from *Bacillus subtilis* (ATCC 6633) represented substantially by the amino acid sequence of SEQ ID NO: 5 and a polypeptide of a subunit of a thermoresistant prenyl diphosphate synthetase from *Bacillus stearothermophilus* (ATCC 10149) represented substantially by the amino acid sequence of SEQ ID NO: 6 (having thermal resistance).

PREFERRED EMBODIMENTS OF THE INVENTION

Hereinbelow, the present invention will be described in more detail with reference to the following Example, which should not be construed as limiting the technical scope of the invention.

EXAMPLE 1

Preparation of Genomic DNA from *Micrococcus luteus*

*M. luteus* B-P 26 was cultured in 6 liters of L-broth (containing 10 g of bacto tryptone, 5 g of bacto yeast extract, 5 g of NaCl and 1 g of glucose per liter) at 30° C. for 24 hours. The culture solution was centrifuged at 7,000 rpm at 4° C. for 15 minutes. The cells were suspended and washed in saline-EDTA (0.15 M NaCl, 0.1 M EDTA, pH 8.0) and then re-centrifuged at 7,000 rpm at 4° C. for 10 minutes.

The cells thus obtained (about 17 g in wet weight) were suspended in 17 ml of saline-EDTA. Then, 1 g of lysozyme was added to the cell suspension and incubated at 37° C. for 30 minutes.

Subsequently, 36 ml of sterilized water, 36 ml of 1 M Tris-HCl buffer (pH 9.0), 12 ml of 5 M NaCl and 12 ml of 10% SDS were added to the cell suspension and suspended well. Then, the resultant suspension was frozen using liquid nitrogen. Thereafter, the frozen suspension was thawed at 60° C. and 1.0 g of lysozyme was added thereto at room temperature. Then, the suspension was re-frozen at −70° C. and re-thawed at 60° C . This freezing-and-thawing was repeated again. The suspension was incubated at 37° C. for 1 hour, and then 400 mg of lysozyme of 3.1 mg of proteinase K were added thereto and incubated at 55° C. for 30 minutes. An equal volume (about 150 ml) of phenol was added thereto and agitated slowly for 20 minutes while ice-cooling. The resultant suspension was centrifuged at 3,000 rpm at 4° C. for 10 minutes and the supernatant was collected. This supernatant was further centrifuged at 3,000 rpm at 4° C. for 30 minutes. The resultant supernatant was dispensed in 15 ml portions into 50 ml conical tubes (Falcon). Two volumes of ethanol was added to each tube gently and mixed gently. The white precipitate of thread-like DNA was wound around a glass rod and dissolved in 36 ml of diluted saline-citrate (0.015 M NaCl, 0.0015 M trisodium citrate), to which 4 ml of concentrated saline-citrate (1.5 M NaCl, 0.15 M trisodium citrate) was added. From the measurement of absorbance (A260), the crude yield was found to be about 44 mg. In order to remove RNA, the following operations were performed. To the DNA solution, 40 ml of diluted saline-citrate was added to give a nucleic acid concentration of about 0.5 mg/ml. Then, RNaseTI and RNaseA were added to give final concentrations of 3.6 µg/ml and 50 µg/ml, respectively, and incubated at 37° C. for 30 minutes. An equal volume of phenol was added thereto and agitated slowly by turning the tube up and down for 10 minutes while ice-cooling the tube. The resultant phenol mixture was centrifuged at 3,000 rpm at 4° C. for 10 minutes, and the aqueous layer was mixed with a mixed solution of phenol and chloroform (1:1).

The resultant solution was centrifuged at 3,000 rpm at 4° C. for 15 minutes, and the aqueous layer was collected. Two volumes of ethanol was added to the aqueous layer to precipitate DNA. After centrifuged at 15,000 rpm at 4° C. for 20 minutes, the precipitate was washed with 70%, 80% and 90% ethanol in this order and finally suspended in 50 ml of TE (10 ml Tris-HCl, 1 mM EDTA, pH 7.4).

From the measurement of absorbance, the yield was found to be 4.95 mg.

EXAMPLE 2

Amplification of FPP Synthetase Gene Fragment (B500) by PCR and Cloning of FPP Synthetase Gene The primers described below were synthesized based on the amino acid sequences of "Gly Gly Lys Arg Ile Arg Pro Leu" (SEQ ID NO: 7) in preserved Region I, "Ser Leu Ile His Asp Asp" (SEQ ID NO: 8) and "Asp Leu Arg Arg Gly Arg Pro" (SEQ ID NO: 9) in preserved Region II, "Leu Ala Gly Asp Gly Leu Leu" (SEQ ID NO: 10) in preserved Region III, "Phe Gln Ile Arg Asp Asp Ile Leu Asp" (SEQ ID NO: 11) and "Gly Lys Pro Val Gly Ser Asp" (SEQ ID NO: 12) in preserved Region VI found among prenyl diphosphate synthetases beyond difference in organism species.

Sense Primers:
P1: SEQ ID NO: 13
P2: SEQ ID NO: 14
P3: SEQ ID NO: 15
Antisense Primers:
N1: SEQ ID NO: 16
N2: SEQ ID NO: 17
N3: SEQ ID NO: 18
N4: SEQ ID NO: 19
N5: SEQ ID NO: 20

A PCR was performed using the genomic DNA described above as a template and the above oligonucleotides as primers.

The PCR was performed in a PCR solution having the composition described below 5 cycles, 1 cycle being at 97° C. for 90 seconds, at 40° C. for 90 seconds and at 72° C. for 120 seconds, followed by 20 cycles, 1 cycle being at 96° C. for 90 seconds, at 55° C. for 90 seconds and at 72° C. for 120 seconds.

| Composition of the PCR Solution: | |
| --- | --- |
| Genomic DNA | 1 µg |
| Tris-HCl (pH 8.3) | 10 mM |
| KCl | 50 mM |
| MgCl$_2$ | 1.5 mM |
| Gelatin | 0.001% (w/v) |
| dNTP mixture | 200 µM each |
| Primers | 0.1 nmol each |
| Ampli Taq DNA Polymerase | 2.5 u |
| (Total volume | 100 µl) |

An approx. 500 bp band (B500) which is specifically amplified with a combination of P1 and N3 was obtained. This DNA fragment was ligated to pT7Blue T-vector (Novagen) to thereby obtain pB500. As a result of the determination of its DNA sequence by the dideoxy method, it was found that the amino acid sequence encoded by B500 has 60.7% homology to the amino acid sequence of FPS from *Bacillus stearothermophilus* in 145 amino acids. The genomic DNA from *M. luteus* B-P 26 was partially digested with Sau3AI. The resultant DNA fragments of 4–8 kbp were inserted into pUC119/BamHI, and *E. coli* strain JM109 was transformed with these plasmids to thereby prepare a genomic library. pB500 was digested with PstI and BamHI and then electrophoresed on agarose gel to thereby cut off and recover DNA fragments. The B500 fragments obtained were labeled using Random Primer Labeling Kit (Takara Shuzo) according to the protocol attached thereto. A library of about 6000 colonies was screened by colony hybridization with labeled B500 fragments as probes to thereby obtain clones hybridizing with B500. The prenyl diphosphate synthetase activity of these clones was measured and their products were analyzed. As a result, one product was confirmed to be an FPP synthetase.

EXAMPLE 3

Southern Hybridization of the Genomic DNA from *M. luteus* B-P 26

(1) Blotting of the Genomic DNA to a Nylon Membrane

The genomic DNA from *M. luteus* B-P 26 prepared in Example 1 was subjected to Southern blotting.

| Genomic DNA | 100 µl (10 µg) |
| --- | --- |
| 10x Buffer | 30 µl |
| Sterilized water | 162 µl |
| Enzyme | 8 µl |

In the above composition, 10 µg of the genomic DNA from *M. luteus* B-P 26 was reacted with one of the restriction enzymes EcoRI(10 U/µl), PstI (100 U/µl) and HindIII (12 U/µl) at 37° C. for 40 hours to allow complete digestion. The reaction solution was treated with phenol-chloroform and then with chloroform. Thereafter, the solution was ethanol-precipitated. The resultant DNA was dried under reduced pressured and then dissolved in 100 µl of TE (10 mM Tris-HCl, 1 mM EDTA, pH 8.0) at a concentration of 350 ng/µl. Three DNA solutions (10 µl each) were electrophoresed on 0.8% agarose gel. For Southern blotting, a plate transfer device, NA-1512 (Nippon Eido K.K.), was used. The restriction enzymes used were commercial enzymes (available from Takara Shuzo, NEB or Boehringer Mannheim).

Figure 3:
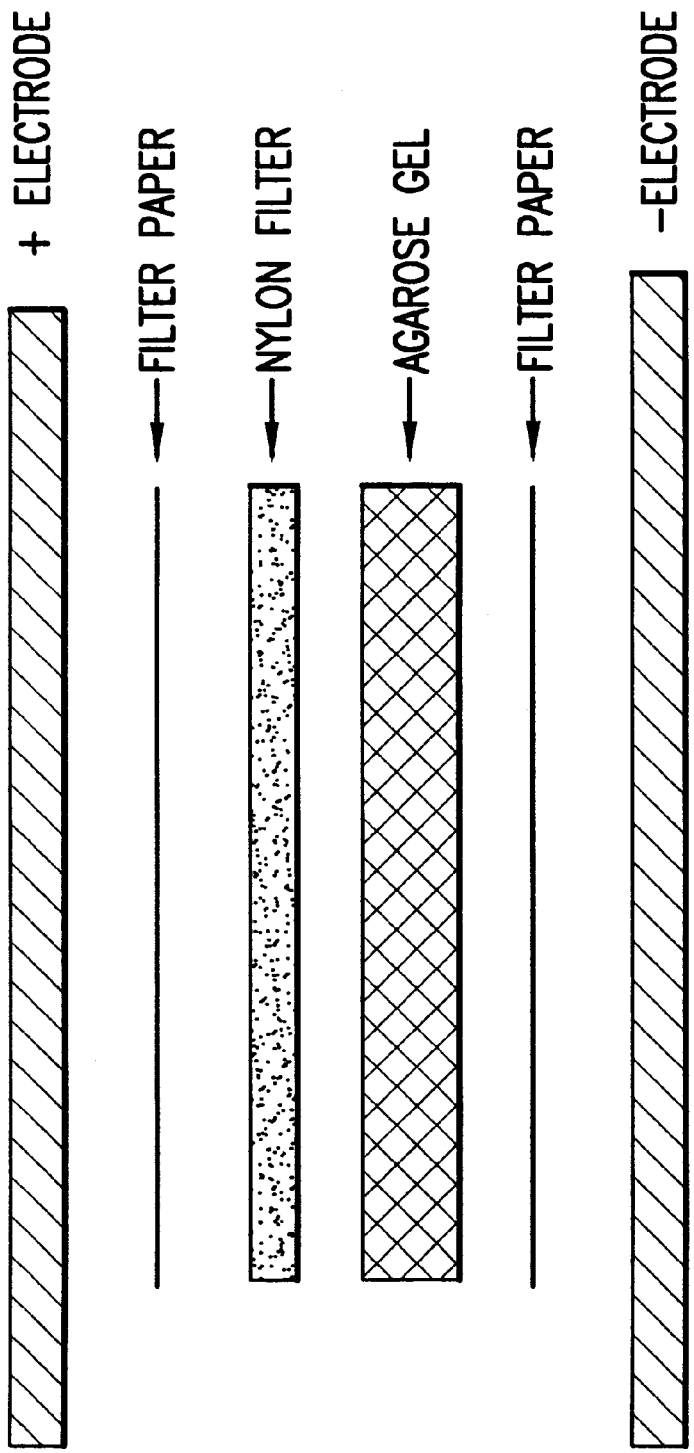
FIG. 3 shows a plate transfer device.

The agarose gel after the electrophoresis of DNA was soaked in a solution containing 1.5 M NaCl and 0.5 M NaOH and shaken slowly for 30 minutes, to thereby denature the DNA. A nylon membrane and a filter paper were cut into the same size as that of the gel and soaked in a solution containing 0.25 M NaOH and 1.5 M NaCl. The agarose gel and the nylon membrane were layered in the plate transfer device as shown in FIG. 3. Then, an electric current (constant) of 150 mA was applied to the device for 60 minutes to thereby transfer the DNA onto the nylon membrane. This membrane was washed with 5×SSC (0.5 M NaCl, 0.075 M sodium citrate), air-dried on a filter paper and then irradiated with UV rays (120 mJ/cm$^2$), to thereby fix the DNA on the membrane.

The thus obtained nylon membrane was used in Southern hybridization.

(2) Preparation of Probes for Southern Hybridization

B500, which is a DNA fragment from the FPS gene, was labeled using random primers (9 mers) and [α-$^{35}$S]dCTP (Amersham). The synthetic oligonucleotides used as probes were labeled by enzymatically transferring to its 5' end the phosphate group at γ position of [γ-$^{32}$P]ATP (Amersham) by means of T4 polynucleotide kinase contained in the following composition.

| 5'-OH oligonucleotides (P1, P2, N3, N4, N5) | 10 pmol |
| --- | --- |
| 10x Kinase buffer | 1 µl |
| [γ-$^{32}$P]ATP (3000 Ci/mmol, 10 µCi/µl) | 3 µl |
| T4 polynucleotide kinase (10 U/µl) | 1 µl |
| Sterilized water to make | 10 µl |
| 10x Kinase buffer: 0.5M Tris-HCl (pH 8.0) | |
| 0.1M MgCl$_2$ | |
| 50 mM DTT solution | |

The above composition was reacted at 37° C. for 30 hours, and then heat-treated at 95° C. for 3 hours to inactivate T4 polynucleotide kinase. The thus obtained end-labeled oligonucleotides were used as probes for Southern hybridization.

Subsequently, hybridization with the labeled probes and washing were performed. Then, autoradiography was performed using a bio-image analyzer manufactured by Fiji Film.

Three identical nylon membrane were prepared and designated No. 1, No. 2 and No. 3. First, No. 1 was hybridized with probe B500, No. 2 with probe N4, and No. 3 with probe N5. Then, autoradiography was performed. Thereafter, the filters were washed to remove the hybridizing probes completely. Thereafter, they were re-hybridized with probes P1, P2 and N3, respectively, and then autoradiographed.

Figure 4A:
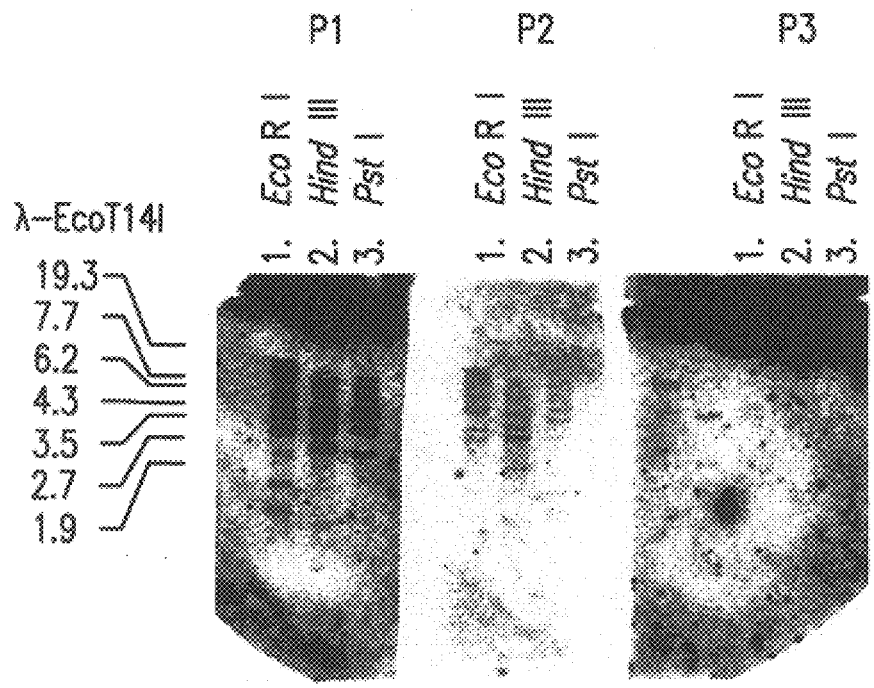
FIG. 4 presents autoradiograms showing the results of Southern hybridization.
Figure 4B:
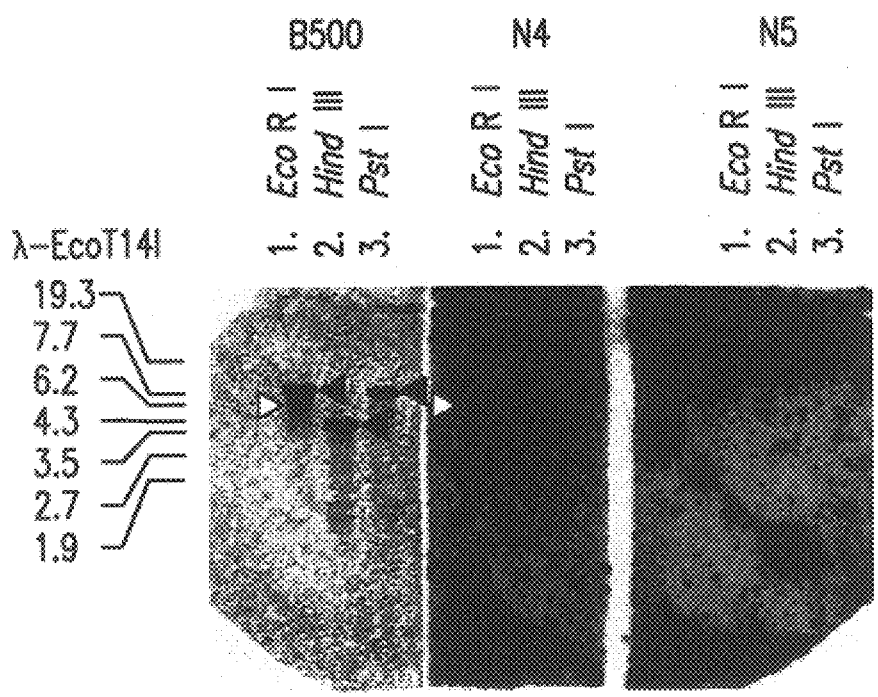

The results are shown in FIG. 4. From these autoradiograms, those bands indicated with mark "▲" appear to be fragments from the FPS gene in view of the strong binding to probe B500. Further, with respect to the genomic DNA digested with EcoRI, a weak band (indicated with mark "Δ"; approx. 4.2 kbp) was confirmed below the FPS band. It is seen that this band of approx. 4.2 kbp is also bound to probe N4 relatively strongly.

Since the FPS gene does not have an EcoRI restriction site in its inside, the FPS gene is never digested with EcoRI to exhibit two bands. Accordingly, there is a possibility that this weakly binding, approx. 4.2 kbp band contains a gene of other prenyl diphosphate synthetase.

Therefore, this DNA fragment of approx. 4.2 kbp was cloned.

(3) Cloning of the DNA Fragment Weakly Hybridizing with Probe B500

4–6 kbp fractions of the EcoRI-digested genomic DNA were cut off from agarose gel and DNA fragments were recovered using The GENECLEAN II Kit (BIO 101).

These DNA fragments were inserted into pUC119 and then E. coli strain JM109 was transformed with the plasmid. Subsequently, colony hybridization was performed.

As a result, three clones hybridizing with every probe were obtained from about 1,200 colonies. These clones were cultured in LB medium. The cells were harvested and disrupted by sonication, to thereby obtain a crude enzyme extract. The measurement of prenyl diphosphate synthetase activity was performed on this crude enzyme solution.

The measurement of activity was performed as follows.

Briefly, positive colonies were cultured in 50 ml of L medium overnight. Then, cells were harvested by centrifugation at 3,000 rpm at 4° C. for 20 minutes and suspended in 3 ml of TE. This suspension was sonicated to disrupt cells. Then, the suspension was centrifuged at 3,000 rpm at 4° C. for 20 minutes to obtain a supernatant. The supernatant was further centrifuged at 15,000 rpm for 5 minutes to thereby obtain a supernatant as a crude enzyme extract. Sonication was performed at an output of 40W with 30% pulse for 5 minutes.

| Crude homogenate | 20 μg |
|---|---|
| Tris-HCl (pH 7.5) | 100 mM |
| MgCl$_2$ | 5 mM |
| FPP | 5 μM |
| [1-$^{14}$C]IPP (54 Ci/mol) | 0.46 μM |
| H$_2$O to make | 1 ml |

The above composition was reacted at 37° C. for 3 hours. To the reaction solution, 3 ml of butanol was added and agitated. The mixture was left stationary or centrifuged to thereby separate into two layers. The butanol layer was recovered. Using 500 μl of this layer, the level of radioactivity in the product was measured with a liquid scintillation counter. Also, 2 ml of the recovered butanol layer was treated with acid phosphatase and subjected to reversed phase thin layer chromatography (TLC), to thereby analyze the product.

| BuOH extract | 2 ml |
|---|---|
| Acetate buffer (pH 5.6) | 1 ml |
| 5% Triton X-100 | 100 μl |
| MeOH | 1 ml |
| Acid phosphatase (1 g/28 ml) | 500 μl |

The above composition was reacted at 37° C. for 14 hours. To the reaction solution, 4 ml of pentane was added and agitated. The mixture was left stationary or centrifuged to thereby separate into two layers. Then, the pentane layer was recovered. The solvent was removed with nitrogen gas, and the remaining material was dissolved in 100 μl of pentane and applied to LKC18 reversed phase thin layer chromatography (Whatman; developing solvent: acetone/water=19/1).

Figure 5:
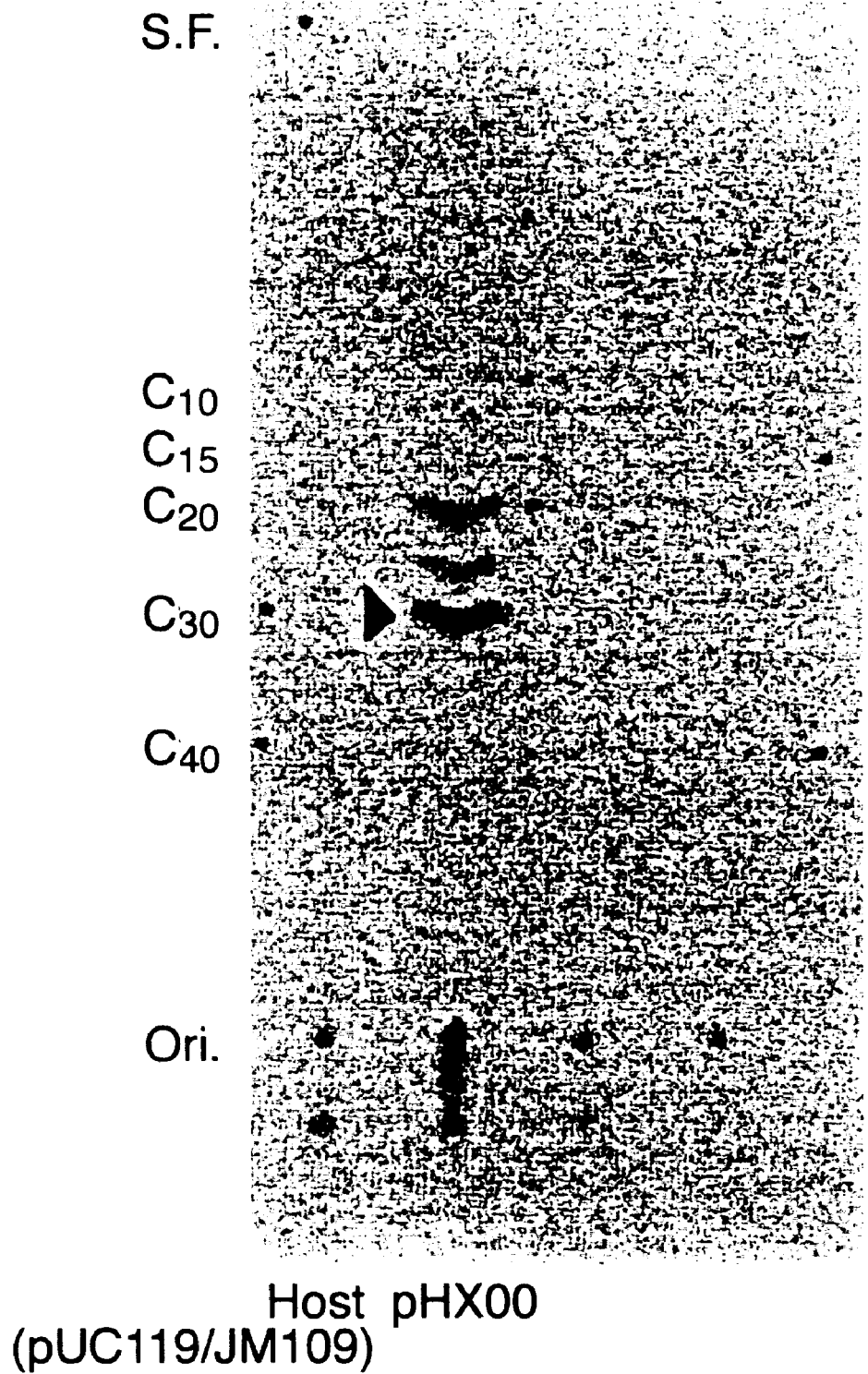
FIG. 5 is a chromatogram showing the results of a reversed phase TLC.

The results are shown in FIG. 5.

From these results, the product was found to be a HexPP.

Thus, a clone containing a HexPP gene was obtained and designated pHX00. Hereinafter, this clone was used in the analysis of DNA sequences.

EXAMPLE 4

Analysis of a Restriction Map and DNA Sequences (1) Preparation of Deletion Clones from pHX00

Figure 6:
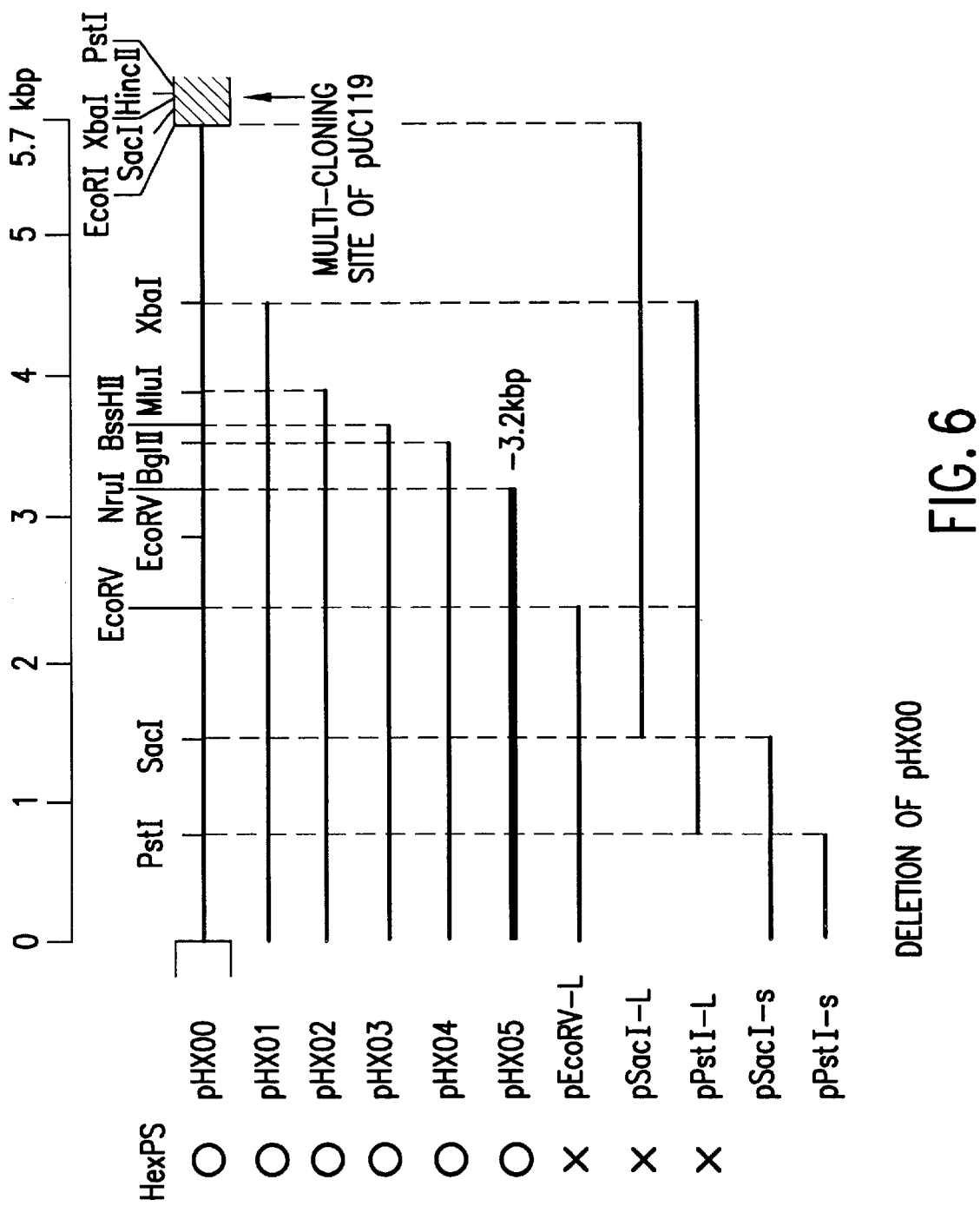
FIG. 6 is a diagram showing a summary of deletion clones.

A restriction map of pHX00 was created and deletion clones were prepared based on the map. Thus, DNA fragments of different length were obtained (FIG. 6). As shown in FIG. 6, fragments pHX01–pHX05 and pEcoRV-L were prepared as follows. First, pHX00 was digested with XbaI, and the digest was cut at the site indicated for each fragment (e.g., MluI site for pHX02 and NruI site for pHX05). The resultant digest was electrophoresed on agarose gel and a DNA fragment having the predicted length was recovered using The GENECLEAN II Kit (BIO 101). Subsequently, the ends of the DNA fragment were blunted with T4 DNA polymerase. Then, a deletion clone of interest was prepared by self ligation.

Fragments pSacI-L and pSacI-s in FIG. 6 represent the two fragments generated by cutting pHX00 with SacI. The longer fragment (containing pUC119) was self-ligated to obtain pSacI-s, and the shorter fragment was ligated to another pUC119 digested with SacI to obtain pSacI-L.

Fragments pPstI-L and pPstI-s in FIG. 6 were obtained in a similar manner from pHX01. In other words, pHX01 was digested with PstI. The longer one of the resultant two fragments was self-ligated to obtain pPstI-s and the shorter one was inserted into the PstI site of another pUC119 to obtain pPstI-L (FIG. 6).

With pSacI-L and pPstI-L, two plasmids of opposite directions of insertion are obtained for each of them. These plasmids of opposite directions were designated pSacI-L-1 and -2 and pPstI-L-1 and -2, respectively.

For each of the deletion clones described above, prenyl diphosphate synthetase activity was measured. As a result, a clone of the minimum length exhibiting activity, pHX05, was obtained (FIG. 6).

Further, deletion clones having serial deletions in the right and the opposite direction of the gene were prepared from pPstI-L-1 and pPstI-L-2 using Deletion Kit for Kilo-sequence (Takara Shuzo) according to the protocol attached to the Kit. Using the thus prepared deletion clones, base sequences were analyzed.

(2) Determination of the DNA Sequence

The deletion clones prepared by the alkali-SDS method was alkali-denatured as described below to prepare a template DNA.

| Template | 32 μl (1.5–2 μg DNA) |
|---|---|
| 2M NaOH | 8 μl |
| Total volume | 40 μl |

The above solution was prepared, agitated gently, and incubated at room temperature for 10 minutes. To the resultant solution, 7 μl of 3 M sodium acetate (pH 4.8) and 4 μl of distilled water were added.

Then, 120 μl of ethanol was added further and mixed. Thereafter, the solution was placed in dry ice for 15 minutes. The solution was centrifuged at 15,000 rpm at 4° C. for 15 minutes to precipitate the DNA, which was washed with 70% ethanol and centrifuged at 15,000 rpm at 4° C. for 10 minutes. The supernatant was discarded. Then, the DNA was dried under reduced pressure and dissolved in 10 μl of distilled water.

Using the thus prepared DNA as a template DNA, analysis of the base sequence was performed by the dideoxy method with T7 Sequencing Kit (Pharmacia) and [α-$^{35}$S]dCTP (Amersham).

The DNA sequence analyzed is shown in SEQ ID NO: 21.

Figure 7:
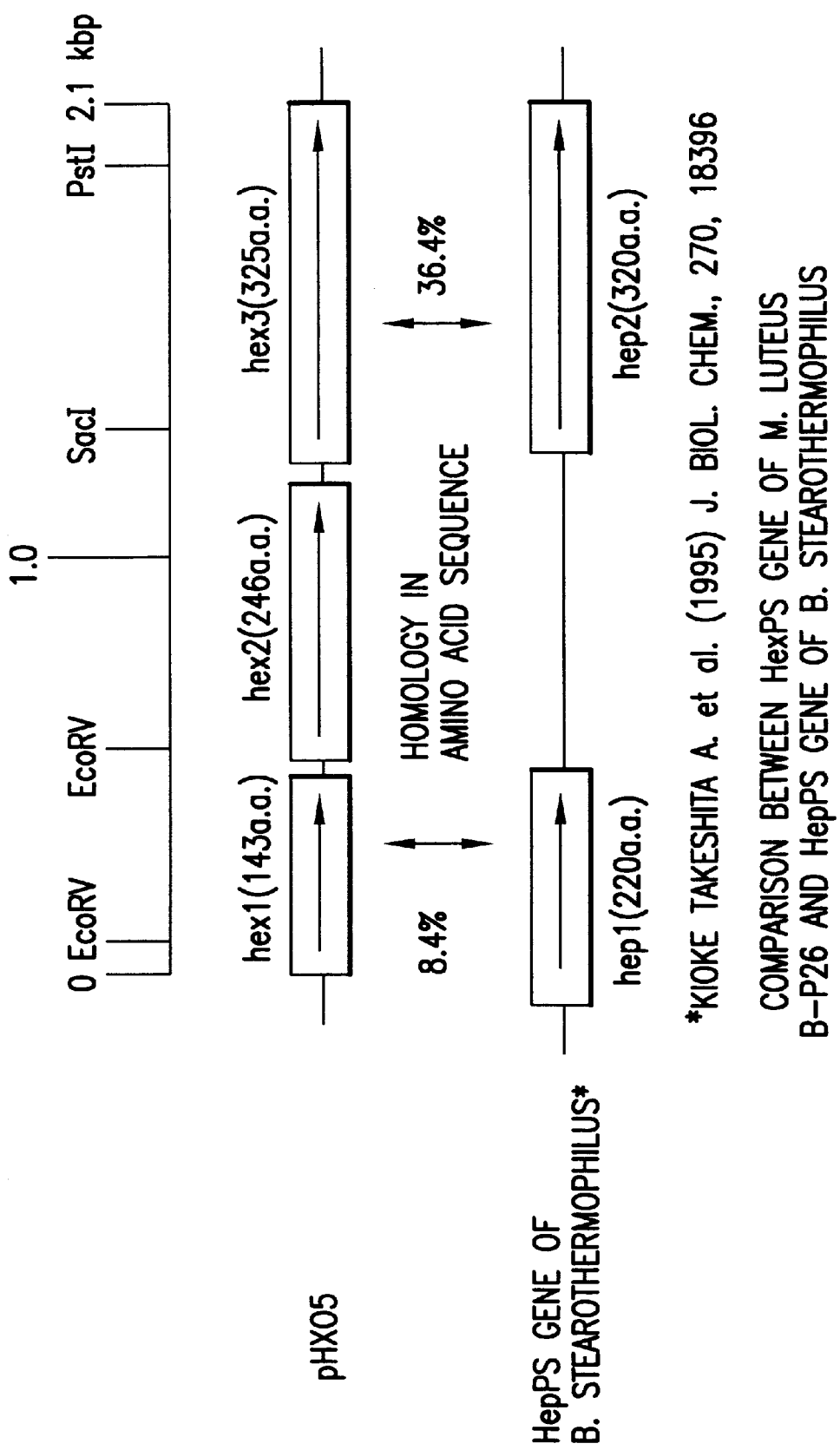
FIG. 7 is a diagram showing the ORFs of the DNA of the present invention.

As a result, it has become clear that pHX05 contains 3 open reading frames coding for proteins. They were designated hex1, hex2 and hex3 from the upstream (FIG. 7).

hex1 codes for a protein composed of 143 amino acids shown in SEQ ID NO: 1. The presumed molecular weight of this protein was 17 kDa. hex2 codes for a protein composed of 246 amino acids shown in SEQ ID NO: 29. The presumed molecular weight of this protein was 28 kDa. The first 23 bases including the initiation codon overlapped with a downstream portion of hex1. hex3 codes for a protein composed of 325 amino acids shown in SEQ ID NO: 2. The presumed molecular weight of this protein was 37 kDa.

The amino acid sequences (Hex1, Hex2 and Hex3) of the proteins encoded by these 3 open reading frames (ORFs) were compared with the amino acid sequences (Hep1 and Hep2) of the proteins encoded by HepPS genes (heP1, hep2) of *Bacillus stearothermophilus*. As a result, Hex3 exhibits 36.4% homology to Hep2 and retains the 7 preserved regions described previously common in prenyl diphosphate synthetases.

On the other hand, Hex1 exhibits only 8.4% homology to Hep1 and is composed of a very small number (i.e., 143) of amino acids whereas Hep1 is composed of 220 amino acids.

The structural genes of the *Bacillus stearothermophilus* HepPS are hep1 and hep2. From the homology to these genes, hex3 was expected to be the structural gene of the HexPS of *M. luteus* B-P 26. However, hex1 and hex2 could not be judged so because they do not exhibit high homology to hep1. Then, the inventor decided to confirm which ORF is the structural gene of the HexPS.

EXAMPLE 5

Measurement of the Activity of Heterodimeric Prenyl Diphosphate Synthetases (1)

(i) Identification of the HexPP Synthetase Gene

Figure 8:
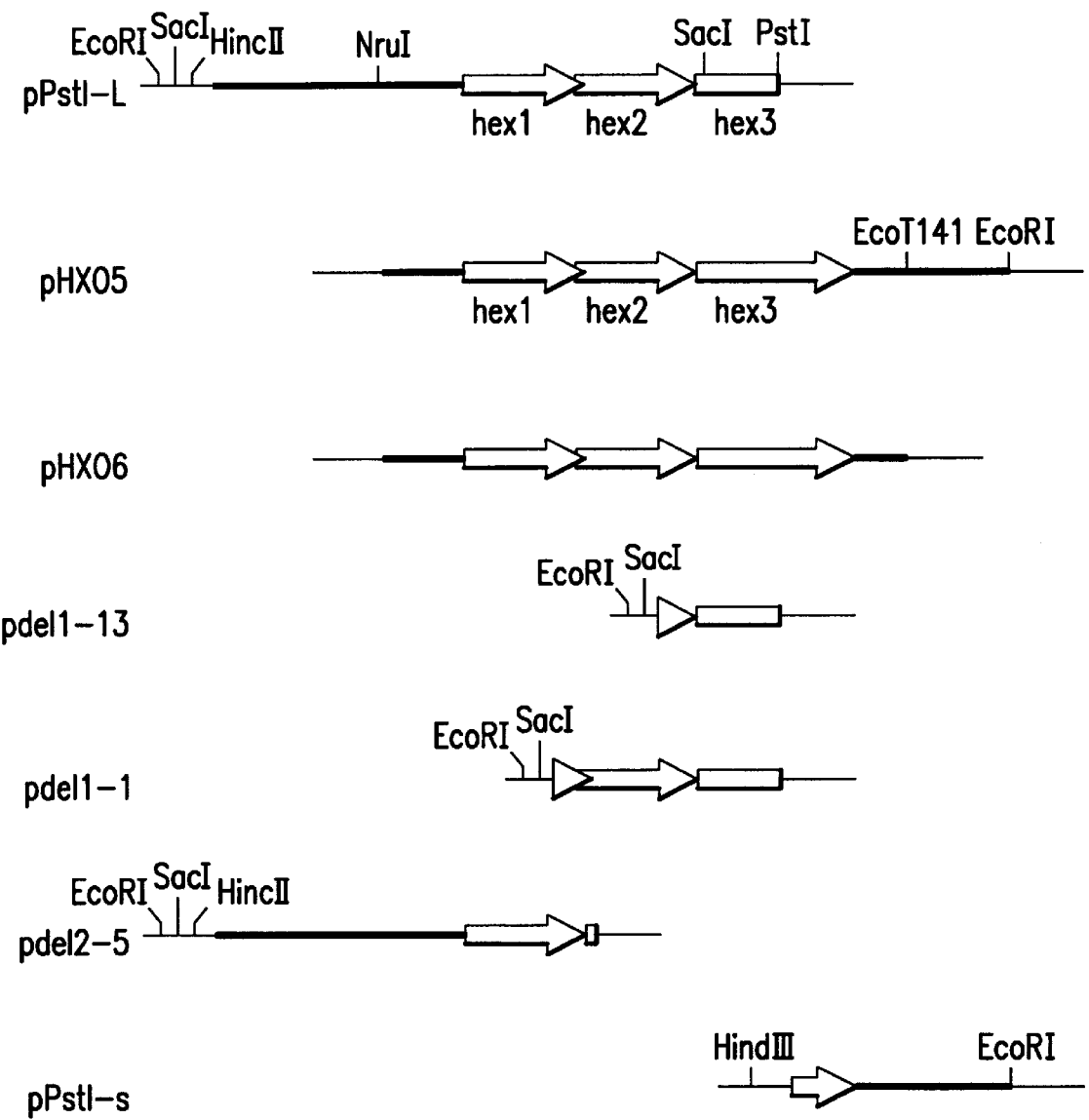
FIG. 8 is a diagram showing a summary of those clones used in the construction of plasmids each having one of the ORFs.
Figure 9:
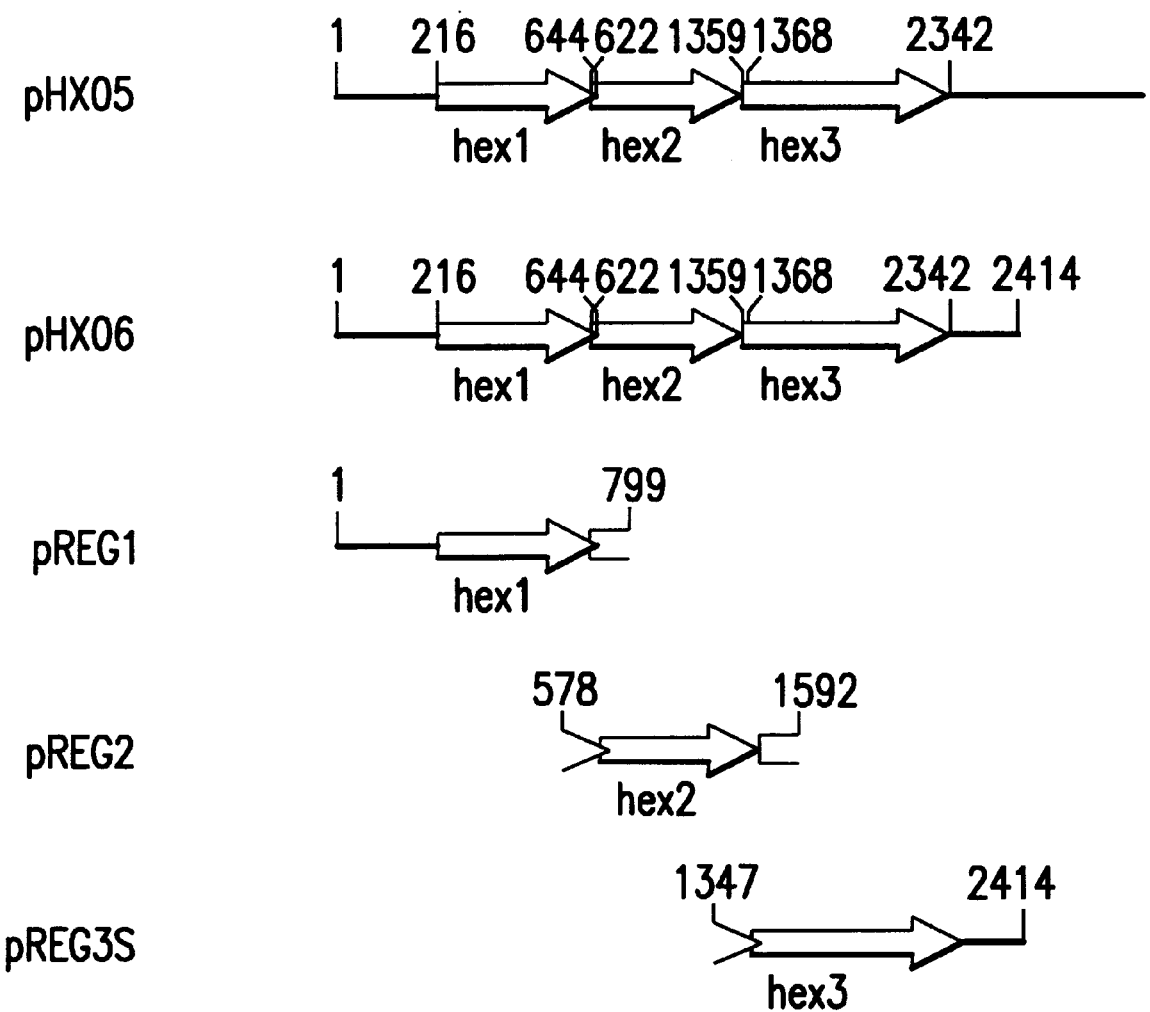
FIG. 9 is a diagram showing plasmids each having one of the ORFs.

In order to prepare a plasmid containing hex1 alone, pde1 2–5 was digested with HincII and NruI and the resultant fragments were self-ligated (FIGS. 8 and 9). Thus, pREG1 was obtained. Similarly, in order to prepare a plasmid containing hex2 alone, SacI-SacI fragment from pde1 1-1 was cut off and inserted into the SacI site of pUC119, to thereby obtain pREG2 (FIGS. 8 and 9).

A plasmid containing hex3 alone was prepared as follows. pde11–13 was digested with EcoRI. After the fragments were blunt-ended, they were further digested with PstI. Further, pPstI-S was digested with HindIII. After the fragments were blunt-ended, they were digested with PstI. These fragments were ligated to obtain pREG3. Since pREG3 contains about 400 bp of hep3 located in its downstream, pREG3 was digested with EcoRI and EcoT14I, and after the ends of the fragments were blunted, the fragments were ligated to obtain pREG3S (FIGS. 8 and 9). "pde1 2–5", "pde1 1–1" and "pde1 1–13" used herein are the deletion clones of pPstI-L described previously which were prepared with Deletion Kit for Kilo-Sequence.

Thus, plasmids each containing one of the three regions (hex1, hex2 and hex3) found in the insert DNA of pHX05 were prepared (FIG. 9).

Since pHX05 containing hex1, hex2 and hex3 includes about 400 bp of hex3 located in its downstream, pHX00 was digested with NruI and EcoT14I and then ligated to HincII-digested pUC119. Of the resultant two clones, one having the same direction of gene as that of pHX05 was selected and designated pHX06 (FIG. 9).

*E. coli* strain JM109 was transformed with above plasmids and enzyme activity was measured as described previously.

Transformants carrying plasmids pREG1, pREG2 and pREG3 containing the hex1, hex2 and hex3 genes, respectively, have been deposited with the National Institute of Bioscience and Human-Technology, Agency of Industrial Science and Technology as follows:

|  | Accession Number |
|---|---|
| pREG1/JM109 | FERM BP-5910 |
| pREG2/JM109 | FERM BP-5911 |
| pREG3S/JM109 | FERM BP-5912 |

(ii) Measurement of Enzyme Activity

A crude enzyme extract was prepared from each of the clones obtained. The enzyme activity of the combinations shown in Table 1 was examined.

Figure 10:
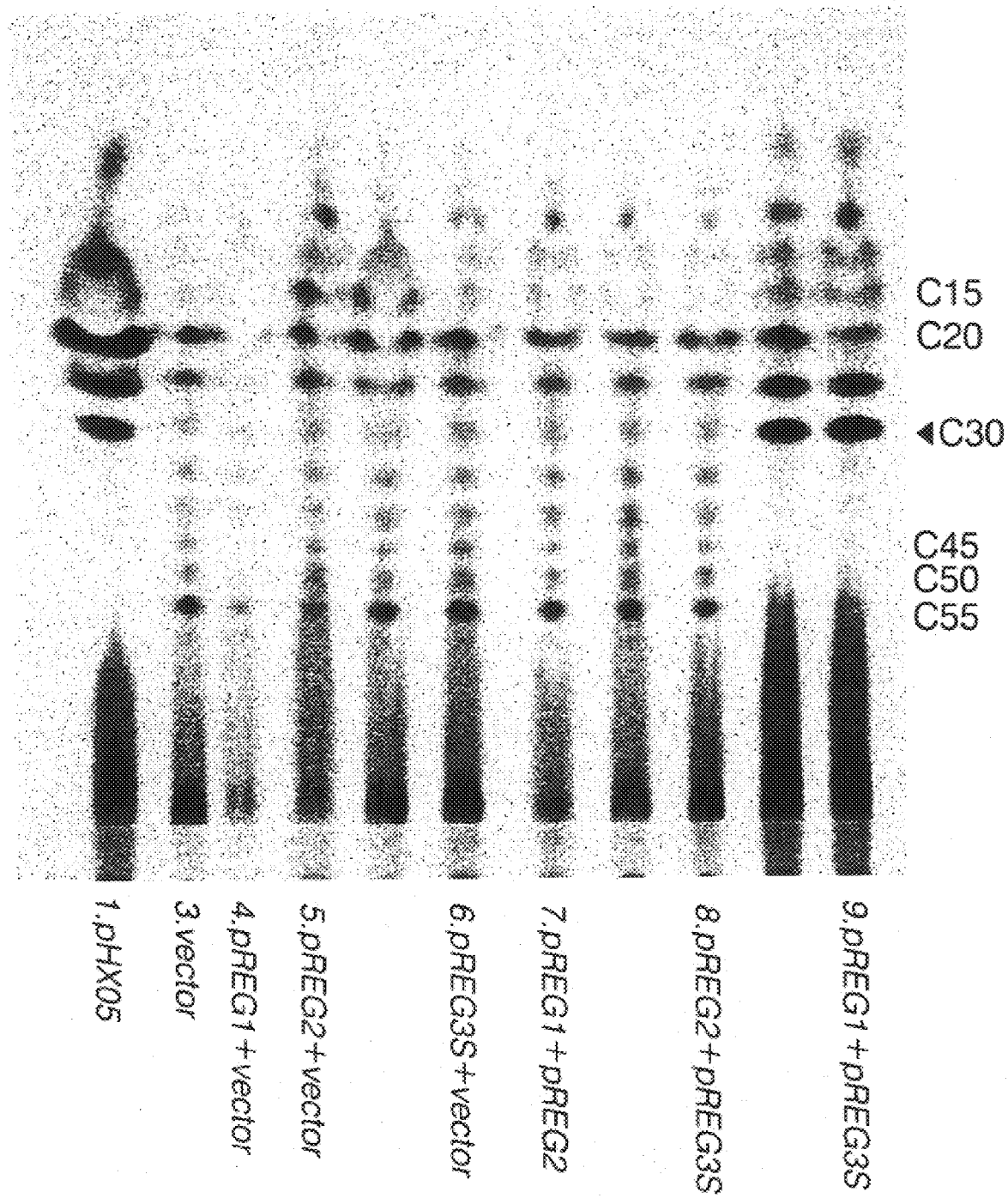
FIG. 10 presents the results of a reversed phase TLC (a chromatogram) showing the enzyme activity of the expression product when two plasmids each having one of the ORFs are combined.

The results are shown in table 1 and FIG. 10.

TABLE 1

| | *M. luteus* | |
|---|---|---|
| Lane Homogenate | | Activity (dpm) |
| 1. JM109/pHX05* | | 2693 |
| 2. JM109/pHX06* | | 2533 |
| 3. JM109/vector* | | 0 |
| 4. JM109/pREG1 + JM109/vector | | 53 |
| 5. JM109/pREG2 + JM109/vector | | 0 |
| 6. JM109/PREG3S + JM109/vector | | 0 |
| 7. JM109/pREG1 + JM109/pREG2 | | 0 |
| 8. JM109/PREG2 + JM109/PREG3S | | 0 |
| 9. JM109/pREG1 + JM109/PREG3S | | 2924 |

1 μg each, *: 2 μg

Lanes 1–9 in FIG. 10 correspond to lanes 1–9 in Table 1.

From Table 1 and FIG. 10, it has been found that HexPS activity is exhibited when the polypeptides encoded by hex1 and hex2 are present at the same time (Table 1, lanes 1, 2 and 9: FIG. 10, lanes 1 and 9). In other words, the enzyme activity is manifested by mixing polypeptide Hex1 [i.e., polypeptide of subunit (A)] with polypeptide Hex3 [i.e., polypeptide of subunit (B)]. From the above results, it is also shown that hex1 and hex3 are the structural genes of the HexPS.

EXAMPLE 6

Measurement of the Activity of Heterodimeric Prenyl Diphosphate Synthetases (2)

(i) Construction of Plasmids Containing a HepPS Gene from *Bacillus subtilis*

From data base search, it has been found that genes exhibiting a high homology to hep1 and hep2 (which are HepPS genes of *Bacillus stearothermophilus*) exist in *Bacillus subtilis*. One corresponding to hep1 is gerC1 and the other corresponding to hep2 is gerC3. Based on the DNA sequences registered in GenBank M80245, the following oligonucleotides were synthesized and used as PCR primers.

| Sense primers |
|---|
| P6': SEQ ID NO: 22 |
| P5': SEQ ID NO: 23 |
| Antisense primers |
| P2': SEQ ID NO: 24 |
| P4': SEQ ID NO: 25 |

*Bacillus subtilis* (ATCC 6633) was cultured in 1 liter of LB medium (containing 10 g of bacto tryptone, 5 g of bacto yeast extract and 10 g of NaCl per liter) at 37° C. until OD600 reached 1. The culture solution was centrifuged at 7,000 rpm at 4° C. for 15 minutes and the cells were harvested.

Genomic DNA from *Bacillus subtilis* was prepared according to the method employed in preparing genomic DNA from *Bacillus stearothermophilus* (Koike-Takeshita, A. et al. (1995) J. Biol. Chem., 270, 18396) and used as a template for PCR.

A PCR was performed using the above genomic DNA as a template and using the oligonucleotides described above as primers.

The PCR was performed 24 cycles in a PCR solution having the composition described below, 1 cycle being at 74° C. for 30 seconds, at 55° C. for 60 seconds and at 72° C. for 60 minutes. Then, the solution was heated to 72° C. and reacted for 7 minutes.

| Composition of the PCR Solution: | |
|---|---|
| Genomic DNA | 1 µg |
| 10x Ampli Taq DNA Polymerase buffer | 10 µl |
| dNTP mixture | 200 µM each |
| Primers | 0.2 µM each |
| Ampli Taq DNA Polymerase | 2.5 U |
| (Total volume | 100 µl) |

For a clone having gerC1, PCR was performed using a combination of P6' and P4' primers. The amplified DNA fragments were digested with NcoI and HindIII and ligated to pTrc99A digested with NcoI and HindIII to thereby prepare pEHA1.

For a clone having gerC3, PCR was performed using a combination of P5' and P2' primers. The amplified DNA fragments were digested with NcoI and BglII and ligated to pTrc99A digested with NcoI and BamHI to thereby prepare pEHA3.

(ii) Construction of Plasmids having hepPS Gene from a *Bacillus stearothermo-philus* (ATCC 10149)

As a clone having hep1, pTLD7 disclosed in Koike-Takeshita, A. et al. (1995) J. Biol. Chem., 270, 18396 was used.

A clone having hep2 was prepared as follows. PCR was performed using pTL6 disclosed in Koike-Takeshita, A. et al. supra as a template and the oligonucleotide described below as primers. The amplified DNA fragments were digested with BspHI and HindIII and ligated to pTrc99A digested with NcoI and HindIII to thereby obtain pHE5.

| Sense primer |
|---|
| HPP10: SEQ ID NO: 26 |
| Antisense primer |
| HPP12: SEQ ID NO: 27 |

(iii) Expression of Proteins

*E. coli* strain JM109 was transformed with the four plasmids pEHA1, pEHA3, pTLD7 and pHE5 described above. Transformants obtained with pEHA1 and pEHA3 were cultured in M9YG medium (1×M9 salt, 0.2% glycerol, 0.2% yeast extract), and transformants obtained with pTLD7 and pHE5 in LB medium. In the late logarithmic growth phase, 1 mM IPTG was added to each medium and cells were cultured for another 3 hours. Thereafter, the culture solution was centrifuged at 5,000 rpm for 20 minutes to thereby harvest cells. Then, about 0.2 g of cells from each transformant were suspended in 1 ml of lysis buffer (25 mM Tris-HCl, 1 mM EDTA, 10 mM 2-mercaptoethanol) and sonicated to disrupt cells. Then, the cell suspension was centrifuged at 15,000 rpm for 5 minutes to obtain the supernatant as a crude enzyme solution. Only those supernatants from transformants obtained with pTLD7 and pHE5 were heat-treated at 55° C. for 15 minutes.

(iv) Measurement of Enzyme Activity

The proteins expressed were mixed in equal amounts in the combinations shown in Table 2 below. Then, HepPS activity of each combination was examined.

The following composition was reacted at 37° C. for 1 hour. The reaction product was extracted with butanol as described previously and used for the measurement of radioactivity and analysis by reversed phase TLC.

| Crude homogenates | 1 µg each |
|---|---|
| Tris-HCl (pH 8.0) | 50 mM |
| MgCl$_2$ | 1 mM |
| NH$_4$Cl | 50 mM |
| 2-Mercaptoethanol | 50 mM |
| FPP | 25 µM |
| [1-$^{14}$C]IPP (54 Ci/mol) | 0.46 µM |

Figure 11:
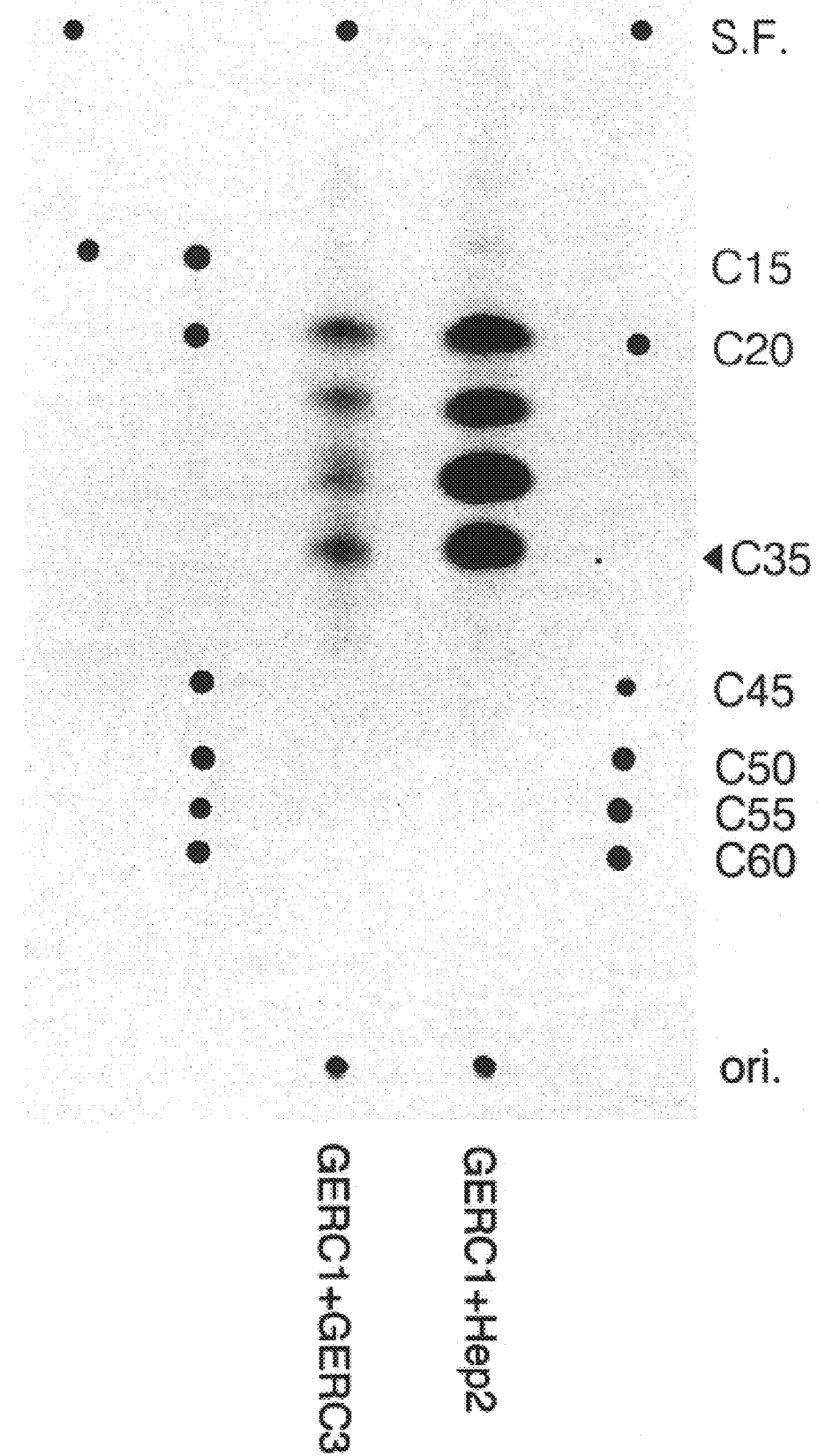
FIG. 11 presents the results of a reversed phase TLC (a chromatogram) showing the enzyme activity when the expression products of a *Bacillus subtilis*-derived gene and a *Bacillus stearothermophilus*-derived gene are combined.

A combination of polypeptides GERC1+GERC3 and another combination of polypeptides GERC1+Hep2 exhibit prenyl diphosphate synthetase activity (Table 2). It was confirmed from the analysis of the reaction products that both combinations synthesize HepPP (FIG. 11).

TABLE 2

Activity of Hybrid Enzymes from *B. subtilis* and *B. stearothermophilus*

| Homogenate | Activity (dpm) |
|---|---|
| GERC1 + GERC3 | 136 |
| GERC1 + Hep2 | 7919 |
| GER1 + GERC3 | 0 |
| Hep1 + Hep2 | 0 |

Protein Amount of homogenate: 1 µg each (v) Comparison of Thermal Stability

Polypeptides GERC1 and GERC3 are derived from *Bacillus subtilis* which is a mesophile. Polypeptide Hep2 is derived from *Bacillus stearothermophilus* which is a moderate thermophilic bacterium. Then, the optimum reaction temperature and the thermal stability of HepPSs obtained from the combinations of GERC1+GERC3 and GERC1+Hep2, respectively, were compared.

Figure 12:
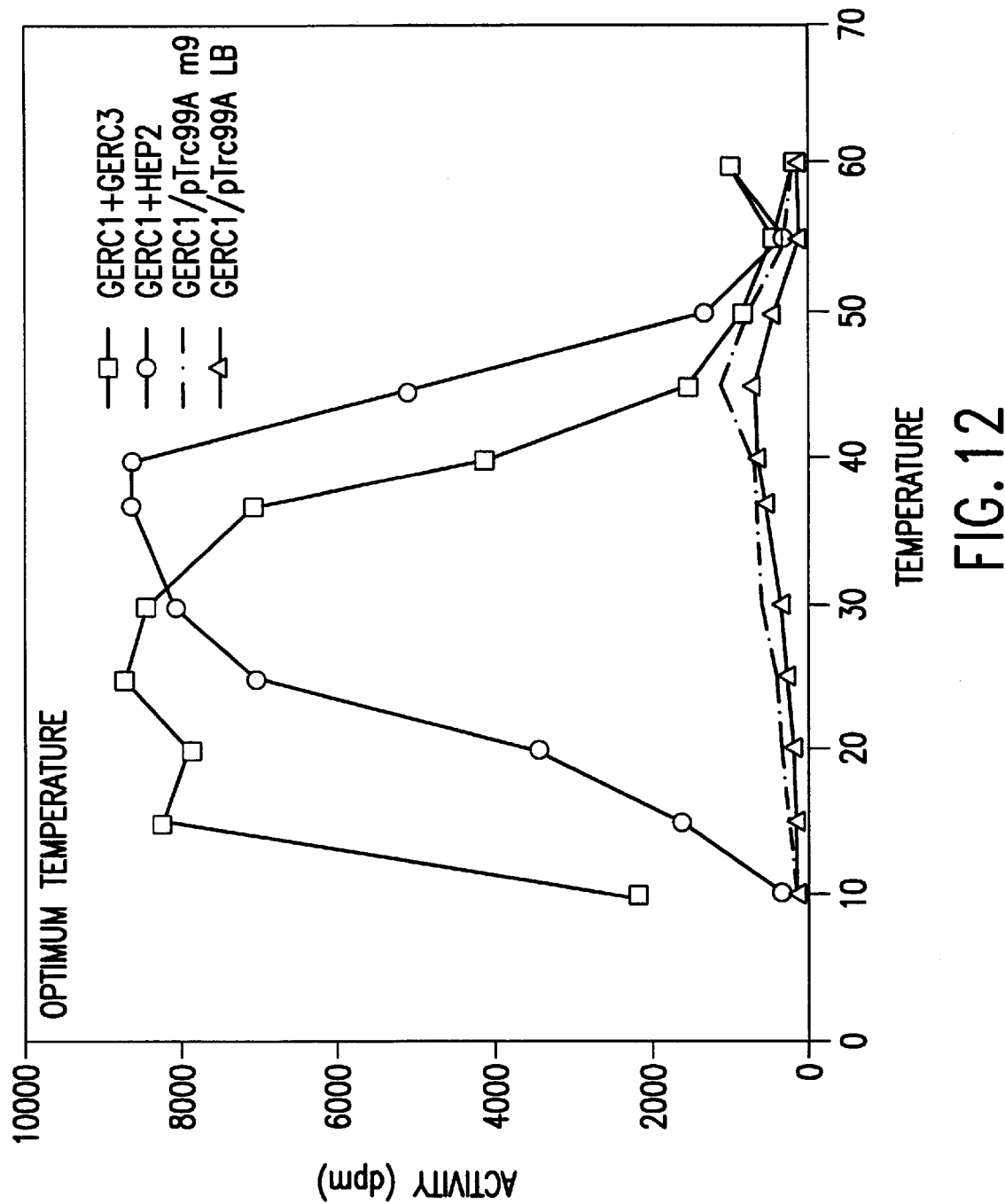
FIG. 12 is a graph showing the optimum temperature for each enzyme.

The combination of GERC1+GERC3 and the combination of GERC1+Hep2 were reacted separately at 10, 15, 20, 25, 30, 37, 40, 45, 50, 55 and 60° C. and the radioactivities of the butanol extracts were compared (FIG. 12). While the optimum reaction temperature of the HepPS resulted from the combination of GERC1+GERC3 is 25° C., that of the HepPS resulted from the combination of GERC1+Hep2 has been raised to 40° C., showing a difference of 15° C.

Figure 13:
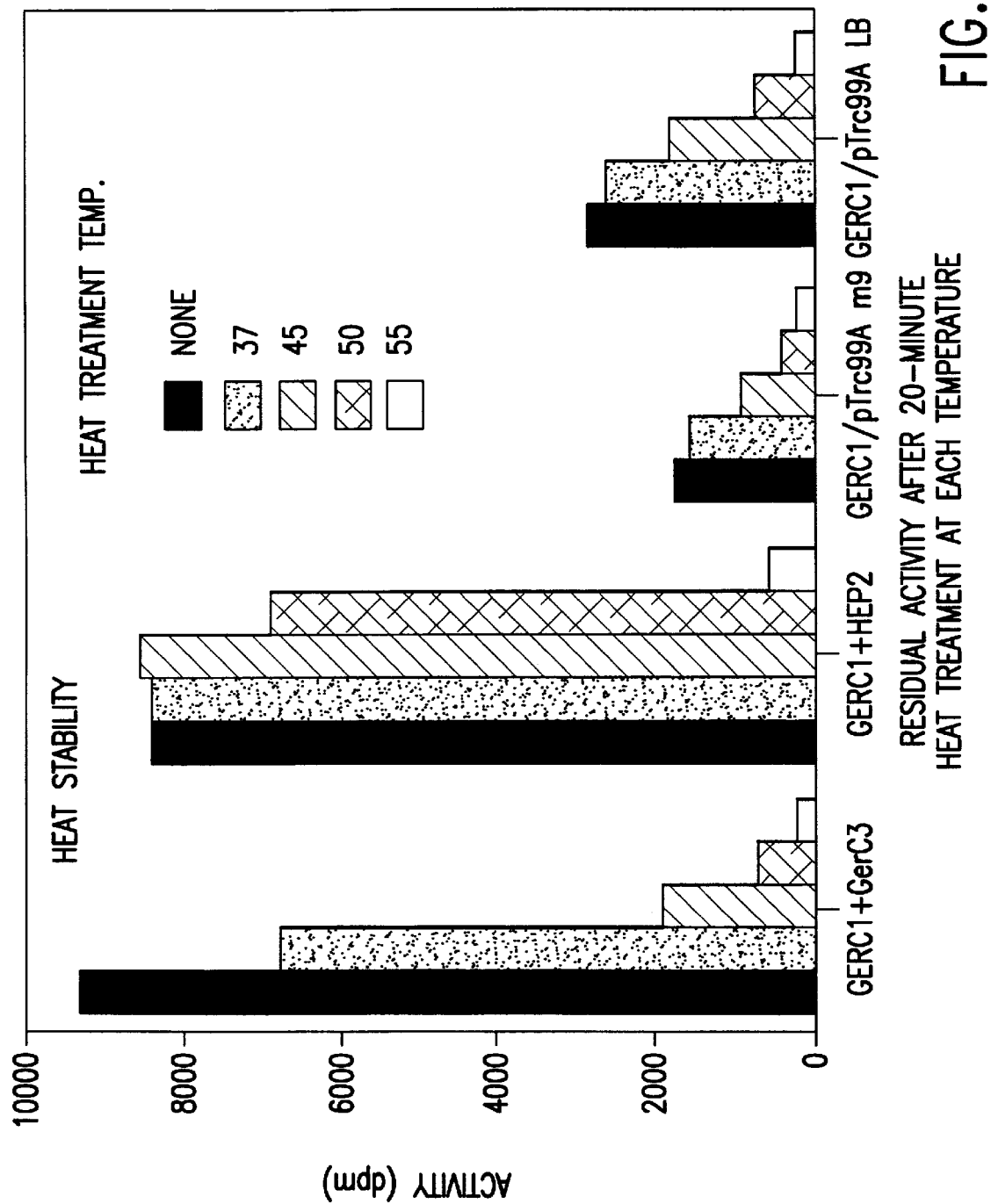
FIG. 13 is a graph showing the residual activity after heat treatment.

Further, the residual activity of both combinations after heat treatment was compared. Crude enzyme solutions were mixed for each combination and heat-treated at 37, 45, 50 and 55° C. for 20 minutes. Thereafter, the reaction solution was reacted at 30° C. for 1 hour and extracted with butanol. The radioactivities of the butanol extracts were compared (FIG. 13).

While the residual activity of the HepPS from GERC1+ GERC3 is 72% after 37° C. treatment, 20% after 45° C. treatment and 7% after 50° C. treatment, the residual activity of the HepPS from GERC1+Hep2 is 102% after 45° C. treatment and 83% after 50° C. treatment.

Although it is known that component II (which appears to correspond to GERC3 of the HepPS from *Bacillus subtilis*) is less stable against heat than component I (which appears to correspond to gerC1) (Fujii, H. et al., (1983) FEBS Lett., 161, 257), the construction of a hybrid enzyme between GERC1 from *Bacillus subtilis* and Hep2 (corresponding to component II) from the moderate thermophilic bacterium *Bacillus stearothermophilus* has rendered thermal stability on this enzyme.

EFFECT OF THE INVENTION

According to the present invention, there are provided a method for producing peptides of prenyl diphosphate synthetases, a method for producing an active type prenyl diphosphate synthetase, a DNA coding for the synthetase, a recombinant vector comprising the DNA and a transformant comprising the vector.

Substances synthesized by the prenyl diphosphate synthetase of the invention are precursors of those substances such as vitamin K and ubiquinones which exist universally in organisms and, thus, they are important physiologically active substances. Therefore, they are of high utility value. Furthermore, the prenyl diphosphate produced by a heterodimeric prenyl diphosphate synthetase is extremely useful since the chain length and structural isomers thereof can be strictly controlled.

What is claimed is:

1. A method for producing an active thermoresistant prenyl diphosphate synthetase which comprises:

separately preparing a first and second polypeptide subunit of prenyl diphosphate synthetase, the first subunit being derived from a first species of Bacillus and the second polypeptide subunit being derived from a second species of Bacillus, the first and second species of Bacillus being different, and mixing the resultant polypeptide subunits to thereby obtain an active thermoresistant enzyme.

2. The method of claim 1 wherein the first species of Bacillus is *Bacillus subtilis* and the second species of Bacillus is *Bacillus stearothermophilus*.

3. The method of claim 2 wherein the polypeptide subunit that is derived from *Bacillus subtilis* has the amino acid sequence of SEQ ID NO:5, and the polypeptide subunit that is derived from *Bacillus stearothermophilus* has the amino acid sequence of SEQ ID NO: 6.

* * * * *

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 143 amino acids
      (B) TYPE: amino acid
      (D) TOPOLOGY: linear (ii) MOLECULE TYPE: protein (xi) SEQUENCE DESCRIPTION: SEQ ID NO: 1:

```
Met Arg Tyr Leu His Lys Ile Glu Leu Glu Leu Asn Arg Leu Thr Ser
                5                  10                  15

Arg Tyr Pro Phe Phe Lys Lys Ile Ala Phe Asp Ala Glu Ile Ile Lys
            20                  25                  30

Leu Val Asp Asp Leu Asn Val Asp Glu Asn Val Lys Cys Ala Ile Val
        35                  40                  45

Ala Ile Asp Thr Ser Met Arg Met Gln Asp Phe Ile Asn Glu Asp Asn
    50                  55                  60

Lys Asp Ser Phe Val Leu Ser Thr Asp Val Leu Ser Ala Leu Phe Tyr
65                  70                  75                  80

Lys Tyr Leu Ser Gln Pro Phe Tyr Gln His Asp Phe Leu Val Leu Thr
                85                  90                  95

Asp Cys Val Ser Arg Ile Asn Glu Leu Lys Ser Ile Arg Ala Thr Ile
            100                 105                 110

Thr Asp Glu Ile Ala Leu His Asn Ile Asn Lys Gln Ile His Tyr Met
        115                 120                 125

Phe Ile Gln Pro Tyr Met Asn Asn Glu Lys Val Val Ser Tyr Glu
    130                 135                 140
```

(2) INFORMATION FOR SEQ ID NO: 2:

(i) SEQUENCE CHARACTERISTICS:
      (A) LENGTH: 325 amino acids
      (B) TYPE: amino acid
      (D) TOPOLOGY: linear (ii) MOLECULE TYPE: protein (xi) SEQUENCE DESCRIPTION: SEQ ID NO: 2:

Met Ile Ala Leu Ser Tyr Lys Ala Phe Leu Asn Pro Tyr Ile Ile Glu
                5                  10                 15

Val Glu Lys Arg Leu Tyr Glu Cys Ile Gln Ser Asp Ser Glu Thr Ile
                20                 25                 30

Asn Lys Ala Ala His His Ile Leu Ser Ser Gly Gly Lys Arg Val Arg
                35                 40                 45

Pro Met Phe Val Leu Leu Ser Gly Phe Leu Asn Asp Thr Gln Lys Asp
    50                  55                 60

Asp Leu Ile Arg Thr Ala Val Ser Leu Glu Leu Val His Met Ala Ser
65                  70                 75                  80

Leu Val His Asp Asp Tyr Ile Asp Asn Ser Asp Met Arg Arg Gly Asn
                85                 90                 95

Thr Ser Val His Ile Ala Phe Asp Lys Asp Thr Ala Ile Arg Thr Gly
                100                105                110

His Phe Leu Leu Ala Arg Ala Leu Gln Asn Ile Ala Thr Ile Asn Asn
                115                120                125

Ser Lys Phe His Gln Ile Phe Ser Lys Thr Ile Leu Glu Val Cys Phe
    130                 135                140

Gly Glu Phe Asp Gln Met Ala Asp Arg Phe Asn Tyr Pro Val Ser Phe
145                 150                 155                160

Thr Ala Tyr Leu Arg Arg Ile Asn Arg Lys Thr Ala Ile Leu Ile Glu
                165                170                175

Ala Ser Cys His Leu Gly Ala Leu Ser Ser Gln Leu Asp Glu Gln Ser
                180                185                190

Thr Tyr His Ile Lys Gln Phe Gly His Cys Ile Gly Met Ser Tyr Gln
                195                200                205

Ile Ile Asp Asp Ile Leu Asp Tyr Thr Ser Asp Glu Ala Thr Leu Gly
    210                 215                220

Lys Pro Val Gly Ser Asp Ile Arg Asn Gly His Ile Thr Tyr Pro Leu
225                 230                 235                240

Met Ala Ala Ile Ala Asn Leu Lys Glu Gln Asp Asp Asp Lys Leu Glu
                245                250                255

Ala Val Val Lys His Leu Thr Ser Thr Ser Asp Asp Glu Val Tyr Gln
                260                265                270

Tyr Ile Val Ser Gln Val Lys Gln Tyr Gly Ile Glu Pro Ala Glu Leu
    275                 280                285

Leu Ser Arg Lys Tyr Gly Asp Lys Ala Lys Tyr His Leu Ser Gln Leu
    290                 295                300

Gln Asp Ser Asn Ile Lys Asp Tyr Leu Glu Glu Ile His Glu Lys Met
305                 310                 315                320

Leu Lys Arg Val Tyr
                325

(2) INFORMATION FOR SEQ ID NO: 3:

(i) SEQUENCE CHARACTERISTICS:
        (A) LENGTH: 432 base pairs
        (B) TYPE: nucleic acid
        (C) STRANDEDNESS: double
        (D) TOPOLOGY: linear (ii) MOLECULE TYPE: genomic DNA (ix) FEATURE:
        (A) NAME/KEY: CDS
        (B) LOCATION:1..429

(xi) SEQUENCE DESCRIPTION: SEQ ID NO: 3:

```
ATG CGT TAT TTA CAT AAA ATT GAA CTA GAA TTA AAC CGA CTT ACA AGT      48
Met Arg Tyr Leu His Lys Ile Glu Leu Glu Leu Asn Arg Leu Thr Ser
                 5                  10                  15

CGA TAT CCA TTT TTC AAA AAA ATT GCA TTT GAT GCT GAA ATC ATA AAG      96
Arg Tyr Pro Phe Phe Lys Lys Ile Ala Phe Asp Ala Glu Ile Ile Lys
             20                  25                  30

CTC GTT GAT GAC CTA AAT GTC GAT GAA AAT GTA AAA TGT GCG ATT GTT     144
Leu Val Asp Asp Leu Asn Val Asp Glu Asn Val Lys Cys Ala Ile Val
         35                  40                  45

GCC ATT GAC ACG AGT ATG CGT ATG CAG GAT TTT ATC AAT GAA GAT AAT     192
Ala Ile Asp Thr Ser Met Arg Met Gln Asp Phe Ile Asn Glu Asp Asn
     50                  55                  60

AAA GAC AGT TTT GTA CTA TCA ACG GAT GTT TTG AGT GCT TTA TTT TAT     240
Lys Asp Ser Phe Val Leu Ser Thr Asp Val Leu Ser Ala Leu Phe Tyr
 65                  70                  75                  80

AAG TAT TTA TCA CAG CCA TTT TAT CAG CAT GAT TTT TTA GTA CTG ACG     288
Lys Tyr Leu Ser Gln Pro Phe Tyr Gln His Asp Phe Leu Val Leu Thr
                 85                  90                  95

GAT TGT GTA AGT CGT ATC AAT GAA TTA AAA TCA ATA AGA GCA ACG ATT     336
Asp Cys Val Ser Arg Ile Asn Glu Leu Lys Ser Ile Arg Ala Thr Ile
             100                 105                 110

ACA GAC GAA ATT GCT TTG CAT AAT ATT AAT AAA CAA ATT CAT TAT ATG     384
Thr Asp Glu Ile Ala Leu His Asn Ile Asn Lys Gln Ile His Tyr Met
         115                 120                 125

TTC ATA CAA CCT TAT ATG AAC AAT GAG AAA GTG GTG TCT TAT GAG TAA     432
Phe Ile Gln Pro Tyr Met Asn Asn Glu Lys Val Val Ser Tyr Glu
     130                 135                 140

(2) INFORMATION FOR SEQ ID NO: 4:

(i) SEQUENCE CHARACTERISTICS:
        (A) LENGTH: 978 base pairs
        (B) TYPE: nucleic acid
        (C) STRANDEDNESS: double
        (D) TOPOLOGY: linear (ii) MOLECULE TYPE: genomic DNA (ix) FEATURE:
        (A) NAME/KEY: CDS
        (B) LOCATION:1..975

(xi) SEQUENCE DESCRIPTION: SEQ ID NO: 4:

ATG ATT GCT TTG AGT TAT AAA GCG TTT TTA AAC CCA TAT ATC ATT GAA      48
Met Ile Ala Leu Ser Tyr Lys Ala Phe Leu Asn Pro Tyr Ile Ile Glu
                 5                  10                  15

GTT GAA AAA AGG TTA TAT GAG TGT ATT CAG AGT GAT TCT GAA ACG ATA      96
Val Glu Lys Arg Leu Tyr Glu Cys Ile Gln Ser Asp Ser Glu Thr Ile
             20                  25                  30

AAC AAG GCG GCA CAC CAT ATT TTA AGT TCA GGA GGA AAG CGC GTA CGT     144
Asn Lys Ala Ala His His Ile Leu Ser Ser Gly Gly Lys Arg Val Arg
         35                  40                  45

CCG ATG TTT GTA TTA TTA AGT GGT TTT CTG AAT GAT ACA CAA AAG GAT     192
Pro Met Phe Val Leu Leu Ser Gly Phe Leu Asn Asp Thr Gln Lys Asp
     50                  55                  60

GAC TTG ATT CGT ACA GCA GTA TCT CTG GAG CTC GTT CAT ATG GCA AGT     240
Asp Leu Ile Arg Thr Ala Val Ser Leu Glu Leu Val His Met Ala Ser
 65                  70                  75                  80

CTC GTT CAT GAT GAT TAC ATC GAT AAT AGT GAT ATG CGT CGT GGT AAT     288
Leu Val His Asp Asp Tyr Ile Asp Asn Ser Asp Met Arg Arg Gly Asn
                 85                  90                  95
```

```
ACT TCG GTT CAT ATA GCT TTT GAT AAA GAC ACA GCA ATT CGC ACA GGA       336
Thr Ser Val His Ile Ala Phe Asp Lys Asp Thr Ala Ile Arg Thr Gly
        100                 105                 110

CAT TTT TTA TTA GCA CGT GCG TTA CAA AAT ATT GCA ACT ATC AAT AAT       384
His Phe Leu Leu Ala Arg Ala Leu Gln Asn Ile Ala Thr Ile Asn Asn
            115                 120                 125

TCG AAA TTC CAT CAA ATT TTT AGT AAA ACG ATA CTT GAA GTT TGT TTT       432
Ser Lys Phe His Gln Ile Phe Ser Lys Thr Ile Leu Glu Val Cys Phe
130                 135                 140

GGT GAA TTT GAC CAG ATG GCA GAT CGA TTT AAT TAT CCT GTA TCC TTT       480
Gly Glu Phe Asp Gln Met Ala Asp Arg Phe Asn Tyr Pro Val Ser Phe
145                 150                 155                 160

ACT GCA TAT TTA AGA CGT ATT AAT CGT AAA ACA GCG ATA CTG ATA GAA       528
Thr Ala Tyr Leu Arg Arg Ile Asn Arg Lys Thr Ala Ile Leu Ile Glu
                165                 170                 175

GCA AGC TGT CAT TTA GGG GCT CTC AGC TCA CAG CTT GAT GAA CAA TCT       576
Ala Ser Cys His Leu Gly Ala Leu Ser Ser Gln Leu Asp Glu Gln Ser
            180                 185                 190

ACA TAT CAT ATA AAA CAA TTT GGG CAT TGT ATT GGA ATG AGT TAT CAA       624
Thr Tyr His Ile Lys Gln Phe Gly His Cys Ile Gly Met Ser Tyr Gln
        195                 200                 205

ATT ATT GAT GAT ATT CTC GAT TAC ACG AGT GAC GAA GCA ACA CTC GGT       672
Ile Ile Asp Asp Ile Leu Asp Tyr Thr Ser Asp Glu Ala Thr Leu Gly
210                 215                 220

AAA CCT GTC GGT AGC GAT ATA AGA AAC GGT CAT ATT ACG TAT CCG CTT       720
Lys Pro Val Gly Ser Asp Ile Arg Asn Gly His Ile Thr Tyr Pro Leu
225                 230                 235                 240

ATG GCC GCT ATC GCT AAT TTG AAA GAG CAA GAT GAC GAT AAA CTT GAA       768
Met Ala Ala Ile Ala Asn Leu Lys Glu Gln Asp Asp Asp Lys Leu Glu
                245                 250                 255

GCA GTT GTT AAA CAT TTA ACA TCA ACA TCA GAT GAT GAA GTG TAT CAA       816
Ala Val Val Lys His Leu Thr Ser Thr Ser Asp Asp Glu Val Tyr Gln
            260                 265                 270

TAT ATT GTT TCG CAA GTT AAA CAA TAT GGA ATT GAA CCT GCA GAA TTG       864
Tyr Ile Val Ser Gln Val Lys Gln Tyr Gly Ile Glu Pro Ala Glu Leu
        275                 280                 285

CTG AGC AGA AAA TAT GGT GAT AAA GCG AAA TAT CAC TTG AGT CAA TTA       912
Leu Ser Arg Lys Tyr Gly Asp Lys Ala Lys Tyr His Leu Ser Gln Leu
290                 295                 300

CAG GAT AGT AAT ATT AAA GAT TAT TTA GAA GAA ATC CAC GAA AAA ATG       960
Gln Asp Ser Asn Ile Lys Asp Tyr Leu Glu Glu Ile His Glu Lys Met
305                 310                 315                 320

TTA AAA CGT GTT TAT TAA                                               978
Leu Lys Arg Val Tyr
                325

(2) INFORMATION FOR SEQ ID NO: 5:

(i) SEQUENCE CHARACTERISTICS:
        (A) LENGTH: 251 amino acids
        (B) TYPE: amino acid
        (D) TOPOLOGY: linear (ii) MOLECULE TYPE: protein (xi) SEQUENCE DESCRIPTION: SEQ ID NO: 5:

Met Gln Asp Ile Tyr Gly Thr Leu Ala Asn Leu Asn Thr Lys Leu Lys
                5                   10                  15

Gln Lys Leu Ser His Pro Tyr Leu Ala Lys His Ile Ser Ala Pro Lys
            20                  25                  30
```

-continued

```
Ile Asp Glu Asp Lys Leu Leu Leu Phe His Ala Leu Phe Glu Glu Ala
            35                  40                  45

Asp Ile Lys Asn Asn Asp Arg Glu Asn Tyr Ile Val Thr Ala Met Leu
    50                  55                  60

Val Gln Ser Ala Leu Asp Thr His Asp Glu Val Thr Thr Ala Arg Val
65                  70                  75                  80

Ile Lys Arg Asp Glu Asn Lys Asn Arg Gln Leu Thr Val Leu Ala Gly
                85                  90                  95

Asp Tyr Phe Ser Gly Leu Tyr Tyr Ser Leu Leu Ser Glu Met Lys Asp
                100                 105                 110

Ile Tyr Met Ile Arg Thr Leu Ala Thr Ala Ile Lys Glu Ile Asn Glu
            115                 120                 125

His Lys Ile Arg Leu Tyr Asp Arg Ser Phe Lys Asp Glu Asn Asp Phe
    130                 135                 140

Phe Glu Ser Val Gly Ile Val Glu Ser Ala Leu Phe His Arg Val Ala
145                 150                 155                 160

Glu His Phe Asn Leu Pro Arg Trp Lys Lys Leu Ser Ser Asp Phe Phe
                165                 170                 175

Val Phe Lys Arg Leu Met Asn Gly Asn Asp Ala Phe Leu Asp Val Ile
                180                 185                 190

Gly Ser Phe Ile Gln Leu Gly Lys Thr Lys Glu Glu Ile Leu Glu Asp
            195                 200                 205

Cys Phe Lys Lys Ala Lys Asn Ser Ile Glu Ser Leu Leu Pro Leu Asn
    210                 215                 220

Ser Pro Ile Gln Asn Ile Leu Ile Asn Arg Leu Lys Thr Ile Ser Gln
225                 230                 235                 240

Asp Gln Thr Tyr His Gln Lys Val Glu Glu Gly
                245                 250

(2) INFORMATION FOR SEQ ID NO: 6:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO: 6:

Met Lys Leu Lys Ala Met Tyr Ser Phe Leu Ser Asp Asp Leu Ala Ala
                5                   10                  15

Val Glu Glu Glu Leu Glu Arg Ala Val Gln Ser Glu Tyr Gly Pro Leu
            20                  25                  30

Gly Glu Ala Ala Leu His Leu Leu Gln Ala Gly Gly Lys Arg Ile Arg
            35                  40                  45

Pro Val Phe Val Leu Leu Ala Ala Arg Phe Gly Gln Tyr Asp Leu Glu
    50                  55                  60

Arg Met Lys His Val Ala Val Ala Leu Glu Leu Ile His Met Ala Ser
65                  70                  75                  80

Leu Val His Asp Asp Val Ile Asp Asp Ala Asp Leu Arg Arg Gly Arg
                85                  90                  95

Pro Thr Ile Lys Ala Lys Trp Ser Asn Arg Phe Ala Met Tyr Thr Gly
                100                 105                 110

Asp Tyr Leu Phe Ala Arg Ser Leu Glu Arg Met Ala Glu Leu Gly Asn
            115                 120                 125
```

```
Pro Arg Ala His Gln Val Leu Ala Lys Thr Ile Val Glu Val Cys Arg
130                 135                 140

Gly Glu Ile Glu Gln Ile Lys Asp Lys Tyr Arg Phe Asp Gln Pro Leu
145                 150                 155                 160

Arg Thr Tyr Leu Arg Arg Ile Arg Arg Lys Thr Ala Leu Leu Ile Ala
                165                 170                 175

Ala Ser Cys Gln Leu Gly Ala Leu Ala Ala Gly Ala Pro Glu Pro Ile
                180                 185                 190

Val Lys Arg Leu Tyr Trp Phe Gly His Tyr Val Gly Met Ser Phe Gln
                195                 200                 205

Ile Thr Asp Asp Ile Leu Asp Phe Thr Gly Thr Glu Glu Gln Leu Gly
210                 215                 220

Lys Pro Ala Gly Ser Asp Leu Leu Gln Gly Asn Val Thr Leu Pro Val
225                 230                 235                 240

Leu Tyr Ala Leu Ser Asp Glu Arg Val Lys Ala Ala Ile Ala Ala Val
                245                 250                 255

Gly Pro Glu Thr Asp Val Ala Glu Met Ala Ala Val Ile Ser Ala Ile
                260                 265                 270

Lys Arg Thr Asp Ala Ile Glu Arg Ser Tyr Ala Leu Ser Asp Arg Tyr
                275                 280                 285

Leu Asp Lys Ala Leu His Leu Leu Asp Gly Leu Pro Met Asn Glu Ala
                290                 295                 300

Arg Gly Leu Leu Arg Asp Leu Ala Leu Tyr Ile Gly Lys Arg Asp Tyr
305                 310                 315                 320

(2) INFORMATION FOR SEQ ID NO: 7:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 7:

Gly Gly Lys Arg Ile Arg Pro Leu
                5

(2) INFORMATION FOR SEQ ID NO: 8:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 8:

Ser Leu Ile His Asp Asp
                5

(2) INFORMATION FOR SEQ ID NO: 9:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 9:
```

Asp Leu Arg Arg Gly Arg Pro
                5

(2) INFORMATION FOR SEQ ID NO: 10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 10:

Leu Ala Gly Asp Gly Leu Leu
                5

(2) INFORMATION FOR SEQ ID NO: 11:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 11:

Phe Gln Ile Arg Asp Asp Ile Leu Asp
                5

(2) INFORMATION FOR SEQ ID NO: 12:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 12:

Gly Lys Pro Val Gly Ser Asp
                5

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 13:

GGHGGHAARC GTAWTCGTCC TTTA                                              24

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 14:

GCNTCNYTRV THCAYGAYGA                                                   20

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 15:

GAYACNCGNC GNGGNCGNCC                                20

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 16:

YTKWCCTCKT CKTAAATCAT C                              21

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 17:

TAATAATSCA TCKCCTGCTA A                              21

(2) INFORMATION FOR SEQ ID NO: 18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 18:

ATCTAAAATA TCATCYTGWA TYTGRAA                       27

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA -continued (xi) SEQUENCE DESCRIPTION: SEQ ID NO: 19:

GTCGCTNCCN ACNGGYTTNC C                                              21

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 20:

NAGRTTYTGN ARNGCYTTRT C                                              21

(2) INFORMATION FOR SEQ ID NO: 21:

(i) SEQUENCE CHARACTERISTICS:
        (A) LENGTH: 2451 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 21:

```
CGAACGTGCT GCACGTAAAG GGCGTAACCC GCAAACTGGT GATGAAATTG AAATCCCAGC      60
AAGCAAAGTT CCAGCATTCA AAGCTGGTAA AGCATTAAAA GATGCAGTTA ATAATTGTA      120
TCTAAAGCCC ATTATGGGCT TTTTTTATTT GTTCTTATAC CATTTTTTAT AAATTATCGT    180
TATAATAATA AAAGGACAAA AATAGAGGTA GATCAATGCG TTATTTACAT AAAAATTGAAC   240
TAGAATTAAA CCGACTTACA AGTCGATATC CATTTTTCAA AAAAATTGCA TTTGATGCTG    300
AAATCATAAA GCTCGTTGAT GACCTAAATG TCGATGAAAA TGTAAAATGT GCGATTGTTG    360
CCATTGACAC GAGTATGCGT ATGCAGGATT TTATCAATGA AGATAATAAA GACAGTTTTG    420
TACTATCAAC GGATGTTTTG AGTGCTTTAT TTTATAAGTA TTTATCACAG CCATTTTATC    480
AGCATGATTT TTTAGTACTG ACGGATTGTG TAAGTCGTAT CAATGAATTA AAATCAATAA    540
GAGCAACGAT TACAGACGAA ATTGCTTTGC ATAAATATTAA TAAACAAATT CATTATATGT   600
TCATACAACC TTATATGAAC AATGAGAAAG TGGTGTCTTA TGAGTAAACA GTTAAATGGA    660
CAGGAAAAAA GTGAGCTTGT ACATAATGTA TTCCAGAATG TATCGACAAA GTATGACCGC    720
CTCAACGATA TCATAAGTTT TAATCAGCAT AAATCCTGGC GTAAATATAC GATGAAACAG    780
ATGAATGTTA AAAAAGGGTC GAAAGCACTT GATGTATGCT GCGGTACAGG CGACTGGACA    840
ATTCAGATGG CACAGGCTGT CGGTAAAAAT GGTCATGTTA TTGGTCTTGA TTTCAGTGAG    900
AATATGTTAA GTGTTGCACA AGGAAAAACG AATCATATAC AAAATATTGA ATTAATTCAT    960
GGTAATGCGA TGGAATTACC ATTTGAAGAT AATATATTTG ATTATACAAC GATTGGTTTT   1020
GGTTTACGTA ACTTACCGGA TTATAAAAAA GGATTAGAAG AAATGTATCG TGTATTAAAA   1080
CCTGGCGGCA TGATTGTTGT TTTAGAAACG AGCCATCCAA CAATGCCAGT ATTTAAACAA   1140
GGTTACAAAT TATATTTCAA ATACGTTATG CCCCTGTTTG GGAAAGTATT TGCTAAGTCT   1200
ATGAAGGAAT ATAGCTGGTT ACAGCAAAGT GCTTTTGAAT TCCTGATAAA GTACACGTTA   1260
GCACTTTTAA TGGCTGAAAC TGGATTTACA CACATTAAAT TTAAAGGTTT TACTGGTGGC   1320
GTGAGTGCGA TGCATCTTGC ATACAAGCCG AAAGAAAAAT AGAATGGATG ATTGCTTTGA   1380
```

-continued

```
GTTATAAAGC GTTTTTAAAC CCATATATCA TTGAAGTTGA AAAAAGGTTA TATGAGTGTA    1440

TTCAGAGTGA TTCTGAAACG ATAAACAAGG CGGCACACCA TATTTTAAGT TCAGGAGGAA    1500

AGCGCGTACG TCCGATGTTT GTATTATTAA GTGGTTTTCT GAATGATACA CAAAAGGATG    1560

ACTTGATTCG TACAGCAGTA TCTCTGGAGC TCGTTCATAT GGCAAGTCTC GTTCATGATG    1620

ATTACATCGA TAATAGTGAT ATGCGTCGTG GTAATACTTC GGTTCATATA GCTTTTGATA    1680

AAGACACAGC AATTCGCACA GGACATTTTT TATTAGCACG TGCGTTACAA AATATTGCAA    1740

CTATCAATAA TTCGAAATTC CATCAAATTT TTAGTAAAAC GATACTTGAA GTTTGTTTTG    1800

GTGAATTTGA CCAGATGGCA GATCGATTTA ATTATCCTGT ATCCTTTACT GCATATTTAA    1860

GACGTATTAA TCGTAAAACA GCGATACTGA TAGAAGCAAG CTGTCATTTA GGGGCTCTCA    1920

GCTCACAGCT TGATGAACAA TCTACATATC ATATAAAACA ATTTGGGCAT TGTATTGGAA    1980

TGAGTTATCA AATTATTGAT GATATTCTCG ATTACGAG TGACGAAGCA ACACTCGGTA      2040

AACCTGTCGG TAGCGATATA AGAAACGGTC ATATTACGTA TCCGCTTATG GCCGCTATCG    2100

CTAATTTGAA AGAGCAAGAT GACGATAAAC TTGAAGCAGT TGTTAAACAT TTAACATCAA    2160

CATCAGATGA TGAAGTGTAT CAATATATTG TTTCGCAAGT TAAACAATAT GGAATTGAAC    2220

CTGCAGAATT GCTGAGCAGA AAATATGGTG ATAAAGCGAA ATATCACTTG AGTCAATTAC    2280

AGGATAGTAA TATTAAAGAT TATTTAGAAG AAATCCACGA AAAAATGTTA AAACGTGTTT    2340

ATTAACAATT GCAAGTAATC CGCTTACAAT GGTAAACTAT TAAGGATTTA TTAAATTACA    2400

AGAGGTAGGA TAACCATGGA AAAACCACTT TTTATGATTA AACCCTGGAC G             2451
```

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 22:

```
GCCATGGAAG ACATCTACGG AACTTTAGCC                                       30
```

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 23:

```
GGTGAATGCC ATGGAATTTA AAATGGCC                                         28
```

(2) INFORMATION FOR SEQ ID NO: 24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: cDNA (xi) SEQUENCE DESCRIPTION: SEQ ID NO: 24:

CGAGATCTCT GCACACCGAA ATCGTAAC                                                                28

(2) INFORMATION FOR SEQ ID NO: 25:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: cDNA (xi) SEQUENCE DESCRIPTION: SEQ ID NO: 25:

AGTCCTGCAT AAAGCTTTAC CCTTC                                                                   25

(2) INFORMATION FOR SEQ ID NO: 26:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: cDNA (xi) SEQUENCE DESCRIPTION: SEQ ID NO: 26:

GGTGAACATC ATGAAGTTAA AGGCG                                                                   25

(2) INFORMATION FOR SEQ ID NO: 27:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: cDNA (xi) SEQUENCE DESCRIPTION: SEQ ID NO: 27:

CGTCCTTGAA AGCTTTAATA ATCCC                                                                   25

(2) INFORMATION FOR SEQ ID NO: 28:

(i) SEQUENCE CHARACTERISTICS:
       (A) LENGTH: 486 base pairs
       (B) TYPE: nucleic acid
       (C) STRANDEDNESS: single
       (D) TOPOLOGY: linear (ii) MOLECULE TYPE: genomic DNA (xi) SEQUENCE DESCRIPTION: SEQ ID NO: 28:

GGTGGCAAGC GCATTAGACC ATTACTTGTT CTGACTACTT TAGATAGTTT AGGTGGCAAT     60

GCACATGACG GTTTACCATT TGGCATTGCG CTTGAAATGA TTCATACGTA TTCTTTAATT    120

CACGATGACT TGCCGGCAAT GGATAATGAT GACTATCGTC GCGGTAAACT CACGAATCAT    180

AAGCGTTTTG ATGAAGCAAC AGCTATACTC GCTGGAGATG CATTGCTCAC TGATGCTTTT    240

CAATGCATTT TAAATACGCA GTTAAACGCA GAAATTAAAT TATCATTGAT TAATTTATTA    300

AGTACTGCTT CTGGATCTAA TGGCATGGTT TACGGCCAAA TGCTCGATAT GCAAGGTGAA    360

CATAAAACAT TGACATTAAA TGAACTGGAA CGTATTCACA TACATAAAAC CGGTGANTTG    420

-continued

```
ATTCGTGCAG CANTTGTAAG TGCAGGTATC ATANTGANTT TTANTGATGC ACAANTGAGC      480

AACTCA                                                                 486
```

(2) INFORMATION FOR SEQ ID NO: 29:

(i) SEQUENCE CHARACTERISTICS:
        (A) LENGTH: 741 base pairs
        (B) TYPE: nucleic acid
        (C) STRANDEDNESS: double
        (D) TOPOLOGY: linear (ii) MOLECULE TYPE: genomic DNA (ix) FEATURE:
        (A) NAME/KEY: CDS
        (B) LOCATION:1..738

(xi) SEQUENCE DESCRIPTION: SEQ ID NO: 29:

```
ATG AGA AAG TGG TGT CTT ATG AGT AAA CAG TTA AAT GGA CAG GAA AAA         48
Met Arg Lys Trp Cys Leu Met Ser Lys Gln Leu Asn Gly Gln Glu Lys
              5                  10                  15

AGT GAG CTT GTA CAT AAT GTA TTC CAG AAT GTA TCG ACA AAG TAT GAC         96
Ser Glu Leu Val His Asn Val Phe Gln Asn Val Ser Thr Lys Tyr Asp
         20                  25                  30

CGC CTC AAC GAT ATC ATA AGT TTT AAT CAG CAT AAA TCC TGG CGT AAA        144
Arg Leu Asn Asp Ile Ile Ser Phe Asn Gln His Lys Ser Trp Arg Lys
     35                  40                  45

TAT ACG ATG AAA CAG ATG AAT GTT AAA AAA GGG TCG AAA GCA CTT GAT        192
Tyr Thr Met Lys Gln Met Asn Val Lys Lys Gly Ser Lys Ala Leu Asp
 50                  55                  60

GTA TGC TGC GGT ACA GGC GAC TGG ACA ATT CAG ATG GCA CAG GCT GTC        240
Val Cys Cys Gly Thr Gly Asp Trp Thr Ile Gln Met Ala Gln Ala Val
 65                  70                  75                  80

GGT AAA AAT GGT CAT GTT ATT GGT CTT GAT TTC AGT GAG AAT ATG TTA        288
Gly Lys Asn Gly His Val Ile Gly Leu Asp Phe Ser Glu Asn Met Leu
                 85                  90                  95

AGT GTT GCA CAA GGA AAA ACG AAT CAT ATA CAA AAT ATT GAA TTA ATT        336
Ser Val Ala Gln Gly Lys Thr Asn His Ile Gln Asn Ile Glu Leu Ile
            100                 105                 110

CAT GGT AAT GCG ATG GAA TTA CCA TTT GAA GAT AAT ATA TTT GAT TAT        384
His Gly Asn Ala Met Glu Leu Pro Phe Glu Asp Asn Ile Phe Asp Tyr
        115                 120                 125

ACA ACG ATT GGT TTT GGT TTA CGT AAC TTA CCG GAT TAT AAA AAA GGA        432
Thr Thr Ile Gly Phe Gly Leu Arg Asn Leu Pro Asp Tyr Lys Lys Gly
    130                 135                 140

TTA GAA GAA ATG TAT CGT GTA TTA AAA CCT GGC GGC ATG ATT GTT GTT        480
Leu Glu Glu Met Tyr Arg Val Leu Lys Pro Gly Gly Met Ile Val Val
145                 150                 155                 160

TTA GAA ACG AGC CAT CCA ACA ATG CCA GTA TTT AAA CAA GGT TAC AAA        528
Leu Glu Thr Ser His Pro Thr Met Pro Val Phe Lys Gln Gly Tyr Lys
                165                 170                 175

TTA TAT TTC AAA TAC GTT ATG CCC CTG TTT GGG AAA GTA TTT GCT AAG        576
Leu Tyr Phe Lys Tyr Val Met Pro Leu Phe Gly Lys Val Phe Ala Lys
            180                 185                 190

TCT ATG AAG GAA TAT AGC TGG TTA CAG CAA AGT GCT TTT GAA TTT CCT        624
Ser Met Lys Glu Tyr Ser Trp Leu Gln Gln Ser Ala Phe Glu Phe Pro
        195                 200                 205

GAT AAG TAC ACG TTA GCA CTT TTA ATG GCT GAA ACT GGA TTT ACA CAC        672
Asp Lys Tyr Thr Leu Ala Leu Leu Met Ala Glu Thr Gly Phe Thr His
    210                 215                 220
```

-continued

| ATT | AAA | TTT | AAA | GGT | TTT | ACT | GGT | GGC | GTG | AGT | GCG | ATG | CAT | CTT | GCA | 720 |
| Ile | Lys | Phe | Lys | Gly | Phe | Thr | Gly | Gly | Val | Ser | Ala | Met | His | Leu | Ala | |
| 225 | | | | 230 | | | | | 235 | | | | | 240 | | |

| TAC | AAG | CCG | AAA | GAA | AAA | TAG | 741 |
| Tyr | Lys | Pro | Lys | Glu | Lys | | |
| | | | | 245 | | | |